(12) United States Patent
Saiki et al.

(10) Patent No.: US 12,070,346 B2
(45) Date of Patent: Aug. 27, 2024

(54) MEDICAL IMAGE DIAGNOSIS APPARATUS AND MEDICAL INFORMATION DISPLAY CONTROLLING DEVICE

(71) Applicant: CANON MEDICAL SYSTEMS CORPORATION, Otawara (JP)

(72) Inventors: Ryusei Saiki, Nasushiobara (JP); Kazuki Gatayama, Otawara (JP); Kusuto Koga, Utsunomiya (JP); Katsuhiko Ishida, Nasushiobara (JP); Tadatsugu Nunome, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 264 days.

(21) Appl. No.: 17/645,809

(22) Filed: Dec. 23, 2021

(65) Prior Publication Data

US 2022/0202384 A1    Jun. 30, 2022

(30) Foreign Application Priority Data

Dec. 25, 2020 (JP) ................................ 2020-217927
Dec. 23, 2021 (JP) ................................ 2021-209715

(51) Int. Cl.
*A61B 6/46* (2024.01)
*G06F 3/0482* (2013.01)
(Continued)

(52) U.S. Cl.
CPC .............. *A61B 6/465* (2013.01); *A61B 6/469* (2013.01); *G06F 3/0482* (2013.01); *G06F 3/04847* (2013.01); *G06F 3/0486* (2013.01)

(58) Field of Classification Search
CPC ......... A61B 6/032; A61B 6/465; A61B 6/464; A61B 6/469; G06F 2203/04803; G06F 3/0482; G06F 3/04847; G06F 3/0486
See application file for complete search history.

(56) References Cited

U.S. PATENT DOCUMENTS 8,712,798 B2 * 4/2014 Gotman ................. A61B 6/563
705/2
8,976,190 B1 * 3/2015 Westerhoff ............. A61B 5/055
345/502

(Continued)

FOREIGN PATENT DOCUMENTS

JP          2019-208741 A    12/2019
WO    WO 2020/090013 A1     5/2020

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

A medical image diagnosis apparatus according to an embodiment includes an X-ray tube and an X-ray detector, an input interface, and processing circuitry. The processing circuitry is configured to cause a protocol selecting screen to be displayed, which includes a first display region used for displaying a plurality of imaging protocols each including at least one scan and a second display region used for displaying a plurality of icons representing a plurality of scans selected from the imaging protocols and being arranged in a sequential order of execution. When a scan condition of the plurality of scans in the second display region is revised, the processing circuitry is configured to change the display the plurality of icons in accordance with the revised scan condition.

12 Claims, 18 Drawing Sheets

(51) Int. Cl.
  *G06F 3/04847* (2022.01)
  *G06F 3/0486* (2013.01)

(56) References Cited

U.S. PATENT DOCUMENTS

| | | | | |
|---|---|---|---|---|
| 10,168,852 | B2* | 1/2019 | Tatebayashi | A61B 6/465 |
| 2011/0052034 | A1* | 3/2011 | Watanabe | G06T 7/0012 |
| | | | | 378/115 |
| 2011/0311026 | A1* | 12/2011 | Lalena | G16H 40/63 |
| | | | | 378/98.5 |
| 2014/0098931 | A1* | 4/2014 | Profio | A61B 6/03 |
| | | | | 345/1.3 |
| 2014/0369466 | A1* | 12/2014 | Yamashita | A61B 6/487 |
| | | | | 378/42 |
| 2015/0063535 | A1* | 3/2015 | Gatayama | A61B 6/545 |
| | | | | 378/19 |
| 2016/0004396 | A1* | 1/2016 | Gulaka | A61B 6/5229 |
| | | | | 715/771 |
| 2016/0143608 | A1* | 5/2016 | Schmied | A61B 8/465 |
| | | | | 600/407 |
| 2016/0166227 | A1* | 6/2016 | Tanaka | A61B 6/563 |
| | | | | 382/132 |
| 2016/0196045 | A1* | 7/2016 | Abe | A61B 6/5294 |
| | | | | 715/765 |
| 2017/0153801 | A1* | 6/2017 | Kim | G06F 40/14 |
| 2017/0163869 | A1* | 6/2017 | Semba | A61B 6/465 |
| 2017/0303884 | A1* | 10/2017 | Takasawa | A61B 6/467 |
| 2021/0153827 | A1* | 5/2021 | Lewis | G06F 3/04847 |

\* cited by examiner

FIG.18

MEDICAL IMAGE DIAGNOSIS APPARATUS AND MEDICAL INFORMATION DISPLAY CONTROLLING DEVICE

CROSS-REFERENCE TO RELATED APPLICATIONS

This application is based upon and claims the benefit of priority from Japanese Patent Application No. 2020-217927, filed on Dec. 25, 2020; the entire contents of which are incorporated herein by reference.

FIELD

Embodiments described herein relate generally to a medical image diagnosis apparatus and a medical information display controlling device.

BACKGROUND

Conventionally, there are some situations where a medical image diagnosis apparatus selects an imaging protocol for a medical examination (hereinafter, simply "examination") from a list containing imaging protocols generated in advance. The imaging protocols in the list are generated in advance as generic imaging protocols for specific examinations on the basis of, for example, regulations in the hospital and/or a radiation dose guideline.

However, depending on medical examination orders (hereinafter, "examination orders") and patients' situations, the list may not always contain an optimal imaging protocol. In those situations, operators need to perform an imaging protocol optimization process, by reading an imaging protocol used as a base from the list and subsequently performing an operation to add a scan or to edit conditions, for example. Under these circumstances, when the imaging protocol optimization process requires time and effort, the throughput of image diagnosis processes using medical image diagnosis apparatuses would be lowered.

BRIEF DESCRIPTION OF THE DRAWINGS

FIG. 18 is a drawing illustrating example (3) of the scan executing screen displayed by the display device according to the embodiment.

DETAILED DESCRIPTION

Figure 1:
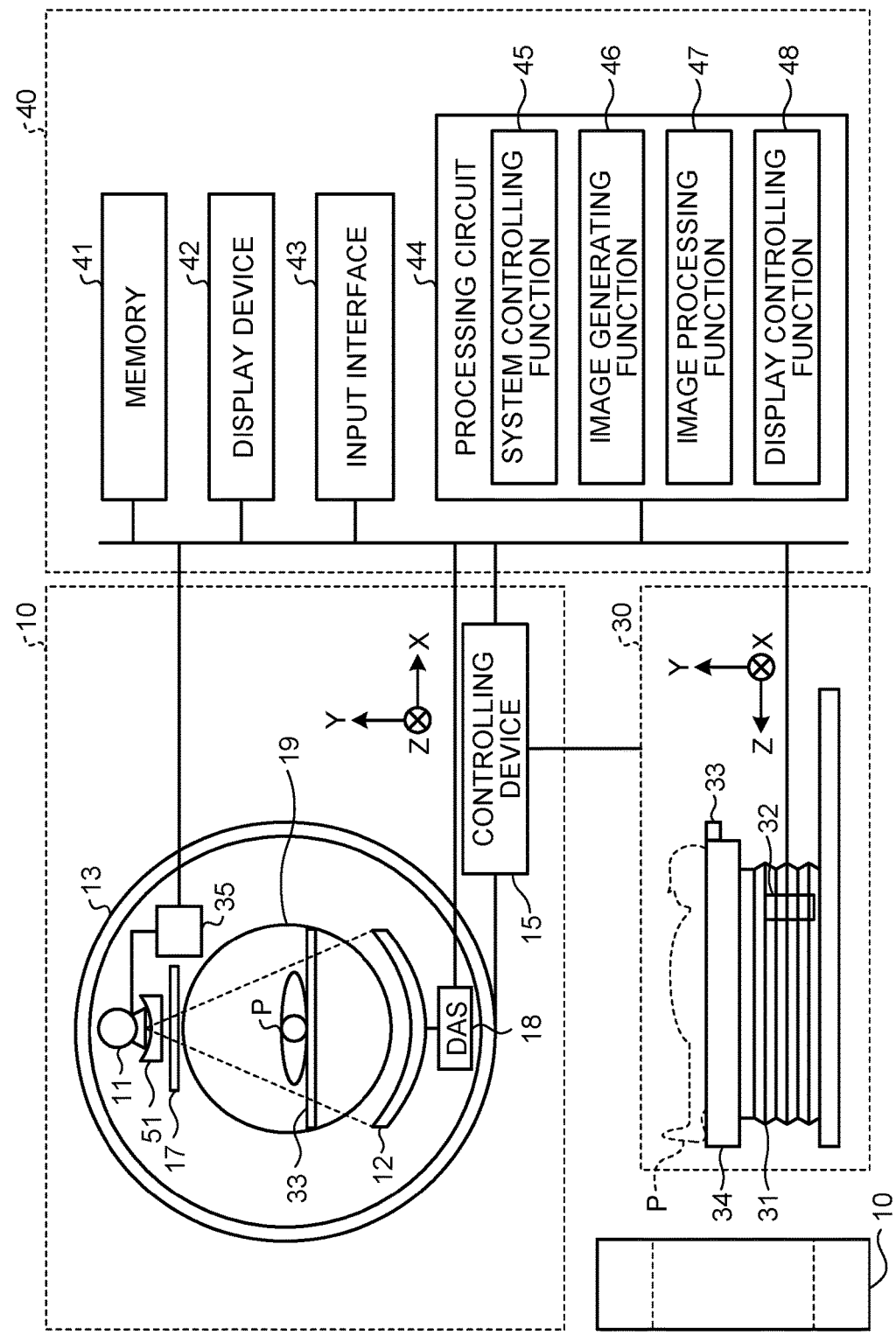
FIG. 1 is a diagram illustrating an exemplary configuration of an X-ray Computed Tomography (CT) apparatus according to an embodiment.

A medical image diagnosis apparatus described in an aspect of the following embodiments includes an X-ray tube and an X-ray detector, an input interface, and processing circuitry. The X-ray tube and the X-ray detector is configured to image an examined subject. The input interface is configured to receive an operation input from an operator. The processing circuitry is configured to cause a display to display a protocol selecting screen including a first display region used for displaying a protocol list indicating a plurality of imaging protocols each including at least one scan and a second display region used for displaying, in response to a first operation input, a plurality of icons representing a plurality of scans selected from the plurality of imaging protocols and being arranged in a sequential order of execution. When a scan condition of the plurality of scans in the second display region is revised in response to a second operation input, the processing circuitry is configured to change the display of the plurality of icons in accordance with the revised scan condition. In response to a third operation input, the processing circuitry is configured to cause a display screen displayed by the display to transition from the protocol selecting screen to a scan executing screen that includes the second display region and is used for executing the plurality of scans as one imaging protocol in the sequential order corresponding to the plurality of icons displayed in the second display region. The processing circuitry is configured to revise the scan condition in response to the second operation input and to control the imaging of the examined subject in accordance with the imaging protocol displayed in the second display region on the scan executing screen.

In the following sections, exemplary embodiments of a medical image diagnosis apparatus and a medical information display controlling device will be explained, with reference to the accompanying drawings. In the description below, some of the constituent elements having the same or substantially the same functions as those previously described with reference to already-explained drawings will be referred to by using the same reference characters, and duplicate explanations will be provided only when necessary. Further, even when depicting the same element, different drawings may use different sizes or scales. Further, some of the constituent elements having the same or substantially the same functions as those previously described with reference to already-explained drawings may be distinguished by having "a", "b", "c" or "d" attached as a suffix. Further, for example, from the viewpoint of ensuring legibility of the drawings, only selected constituent elements may have reference characters attached thereto in the description of the drawings. Even when some of the constituent elements have the same or substantially the same functions as those previously described with reference to already-explained drawings, no reference characters may be attached thereto.

An embodiment of the present disclosure discusses, as an example, an X-ray computed tomography (CT) apparatus serving as a medical image diagnosis apparatus and a medical information display controlling device. FIG. 1 is a diagram illustrating an exemplary configuration of an X-ray CT apparatus 1 according to the embodiment. The X-ray CT apparatus 1 is configured to have X-rays emitted from an X-ray tube 11 onto an examined subject (hereinafter, "patient") P and to have the emitted X-rays detected by an X-ray detector 12. The X-ray CT apparatus 1 is configured to generate CT image (medical image) data related to the patient P, on the basis of an output from the X-ray detector 12.

As illustrated in FIG. 1, the X-ray CT apparatus 1 includes a gantry 10, a table 30, and a console 40. For the sake of convenience in the explanation, FIG. 1 depicts the gantry 10 in multiple locations. The gantry 10 is a scan device having a configuration used for performing an X-ray CT imaging process on the patient P. The table 30 is a conveyance device on which the patient P undergoing the X-ray CT imaging process is placed and which is used for determining the position of the patient P. The console 40 is a computer configured to control the gantry 10. For example, the gantry 10 and the table 30 are provided in a CT examination room, whereas the console 40 is provided in a control room adjacent to the CT examination room. The gantry 10, the table 30, and the console 40 are communicably connected to one another in a wired or wireless manner. In the present example, the gantry 10 and the table 30 are examples of the imaging unit.

In this situation, the console 40 does not necessarily have to be provided in the control room. For example, the console 40 may be provided in the same room with the gantry 10 and the table 30. Alternatively, the console 40 may be incorporated in the gantry 10.

In the present embodiments, the rotation axis of a rotating frame 13 in a non-tilted state or the longitudinal direction of a tabletop 33 of the table 30 is defined as a Z-axis direction, while the axial direction orthogonal to the Z-axis direction and parallel to a floor surface is defined as an X-axis direction, and the axial direction orthogonal to the Z-axis direction and perpendicular to the floor surface is defined as a Y-axis direction.

In this situation, for example, the X-ray CT apparatus 1 is connected to other apparatuses and devices via an intra-hospital Local Area Network (LAN) installed in the hospital so as to be able to directly or indirectly communicate with one another. For example, the X-ray CT apparatus 1 is connected to a Picture Archiving and Communication System (PACS) server configured to store therein medical images and to process medical images, as well as to other medical image diagnosis apparatuses, a terminal device used by a responsible medical doctor to view images, and the like. The apparatuses and devices are configured to transmit and receive medical images and the like to and from one another according to a Digital Imaging and Communication in Medicine (DICOM) standard, for example.

Further, to a system including the apparatuses and the devices described above, a Hospital Information System (HIS) and/or a Radiology Information System (RIS) may be introduced, so as to manage various types of information. For example, in the system, an examination order generated by the terminal device can be transmitted to any of the medical image diagnosis apparatuses and the like. Each of the medical image diagnosis apparatuses is configured to obtain patient information either from the examination order directly received from the terminal device or from a patient list (a modality work list) corresponding to each modality and having been generated by the PACS server that received the examination order.

As illustrated in FIG. 1, the gantry 10 includes the X-ray tube 11, the X-ray detector 12, the rotating frame 13, an X-ray high-voltage device 14, a controlling device 15, a wedge 16, a collimator 17, and a data acquiring circuit (a Data Acquisition System [DAS]) 18.

The X-ray tube 11 is a vacuum tube including a negative pole (a filament) configured to generate thermo electrons and a positive pole (a target) configured to generate X-rays upon collisions of the thermo electrons. The X-ray tube 11 is configured to radiate X-rays onto the patient P, by having the thermo electrons emitted from the negative pole toward the positive pole, by using high voltage supplied from the X-ray high-voltage device 14. In the present example, the X-ray tube 11 is an example of an X-ray generating unit. By switching the voltage supplied by the X-ray high-voltage device 14 in correspondence with a predetermined number of views while the X-rays are being emitted, it is possible to realize a so-called dual-energy CT imaging process. In the present embodiments, the X-ray CT apparatus 1 does not necessarily have to be able to realize dual-energy CT imaging processes. The X-ray CT apparatus 1 may be configured to be able to realize only normal single-energy CT imaging processes. Alternatively, the X-ray CT apparatus 1 may be configured to be able to realize not only dual-energy CT imaging processes, but also multi-energy CT imaging processes in which data processing is performed on three or more types of energy.

The X-ray detector 12 is configured to detect X-rays that were emitted from the X-ray tube 11 and have passed through the patient P and is configured to output an electrical signal corresponding to a detected radiation amount of X-rays to the DAS 18. The X-ray detector 12 includes, for example, rows of X-ray detecting elements in each of which a plurality of X-ray detecting elements are arranged in a channel direction along an arc while being centered on a focal point of the X-ray tube 11. For example, the X-ray detector 12 has a structure in which the plurality rows each having a plurality of X-ray detecting elements disposed in the channel direction are arranged in a slice direction (a row direction). In the present example, the X-ray detector 12 is an example of an X-ray detecting unit.

Further, the X-ray detector 12 is, for example, an indirect-conversion type detector including a grid, a scintillator array, and an optical sensor array. The scintillator array includes a plurality of scintillators. The scintillators each include a scintillator crystal that outputs light in a light quantity corresponding to the amount of X-rays becoming incident thereto. The grid is arranged on a surface of the scintillator array that is positioned on the X-ray incident side and includes an X-ray blocking plate having a function of absorbing scattered X-rays. The grid may be referred to as a collimator (a one-dimensional collimator or a two-dimensional collimator) in some situations. The optical sensor array has a function of converting the light quantity of the light from the scintillators into corresponding electrical signals. As optical sensors, Photomultiplier Tubes (PMTs) may be used, for example.

Alternatively, the X-ray detector 12 may be a detector of a direct-conversion type that includes a semiconductor element configured to convert X-rays becoming incident thereto into an electrical signal.

The rotating frame 13 is an annular frame configured to support the X-ray tube 11 and the X-ray detector 12 so as to oppose each other and configured to rotate the X-ray tube 11 and the X-ray detector 12 via the controlling device 15 (explained later). An opening part 19 of the rotating frame 13 is set with a Field of View (FOV). For example, the rotating frame 13 is a cast product using aluminum as a material thereof. In addition to the X-ray tube 11 and the X-ray detector 12, the rotating frame 13 may also further support the X-ray high-voltage device 14, the wedge 16, the collimator 17, the DAS 18, and the like. Also, the rotating frame 13 may also further support various elements that are not illustrated in FIG. 1. In the present example, the rotating frame 13 is an example of a rotating unit.

The X-ray high-voltage device 14 includes a high-voltage generating device and an X-ray controlling device. The high-voltage generating device includes electric circuits such as a transformer and a rectifier and is configured to generate the high voltage to be applied to the X-ray tube 11 and a filament current to be supplied to the X-ray tube 11. The X-ray controlling device is configured to control output voltage in accordance with the X-rays emitted by the X-ray tube 11. The high-voltage generating device may be of a transformer type or an inverter type. The X-ray high-voltage device 14 may be provided for the rotating frame 13 within the gantry 10 or may be provided for a fixed frame (not illustrated) within the gantry 10. The fixed frame is a frame configured to rotatably support the rotating frame 13. In the present example, the X-ray high-voltage device 14 is an example of an X-ray high-voltage unit.

The controlling device 15 includes: a driving mechanism such as a motor and an actuator; and a processing circuit including a processor configured to control the driving mechanism, as well as a memory, and the like. The controlling device 15 is configured to control operations of the gantry 10 and the table 30, by receiving input signals from the input interface 43, an input interface provided for the gantry 10, and the like. For example, upon receipt of the input signals, the controlling device 15 is configured to exercise control so as to rotate the rotating frame 13, to exercise control so as to tilt the gantry 10, and to exercise control so as to bring the table 30 into operation.

The control to tilt the gantry 10 is realized as a result of the controlling device 15 rotating the rotating frame 13 on an axis extending parallel to the X-axis direction, according to inclination angle (tilt angle) information input by an input interface attached to the gantry 10. The controlling device 15 may be provided for the gantry 10 or may be provided for the console 40.

The wedge 16 is a filter used for adjusting the amount of the X-rays emitted from the X-ray tube 11. More specifically, the wedge 16 is a filter configured to pass and attenuate the X-rays emitted from the X-ray tube 11, so that the X-rays radiated onto the patient P from the X-ray tube 11 have a predetermined distribution. For example, the wedge 16 may be a wedge filter or a bow-tie filter and is structured by processing aluminum or the like so as to realize a predetermined target angle and a predetermined thickness.

The collimator 17 is configured to limit an emission range of the X-rays that have passed through the wedge 16. The collimator 17 is configured to slidably support a plurality of lead plates that block the X-rays and to adjust the form of slits formed by the plurality of lead plates. The collimator 17 may be referred to as an X-ray limiter.

The DAS 18 is configured to read the electrical signals corresponding to the radiation amounts of the X-rays detected by the X-ray detector 12, from the X-ray detector 12. The DAS 18 is configured to acquire detection data having digital values corresponding to the radiation amounts of the X-rays over a view time period, by amplifying the read electrical signals and integrating (adding up) the electrical signals over the view time period. The detection data may be referred to as projection data. For example, the DAS 18 is realized by using an Application Specific Integrated Circuit (ASIC) having installed therein a circuit element capable of generating the projection data. The projection data is transferred to the console 40 via a contactless data transfer device or the like. In the present example, the DAS 18 is an example of a data acquiring unit.

The detection data generated by the DAS 18 is transmitted via optical communication, from a transmitter including a Light Emitting Diode (LED) and being provided for the rotating frame 13, to a receiver including a photodiode and being provided in a non-rotating part (e.g., the fixed frame; not illustrated in FIG. 1) of the gantry 10, so as to be transferred to the console 40. In this situation, the method for transmitting the data from the rotating frame 13 to the non-rotating part of the gantry 10 does not necessarily have to be optical communication. It is acceptable to adopt any contactless data transfer method. Alternatively, it is also acceptable to adopt a data transfer method involving contact.

The table 30 is a device on which the patient P to be scanned is placed and which is configured to move the patient P. The table 30 includes a base 31, a table driving device 32, the tabletop 33, and a supporting frame 34. The base 31 is a casing configured support the supporting frame 34 so as to be movable in vertical directions. The table driving device 32 is a driving mechanism configured to move the tabletop 33 in the longitudinal direction (the Z-axis direction) of the tabletop 33 and includes a motor and an actuator or the like. The tabletop 33 is a board on which the patient P is placed. The tabletop 33 is provided on the top face of the supporting frame 34. The tabletop 33 is able to protrude from the table 30 toward the gantry 10 to make it possible to image the whole body of the patient P. For example, the tabletop 33 is formed by using Carbon Fiber Reinforced Plastic (CFRP) having excellent X-ray permeability and physical properties such as rigidity and strength. Further, for example, the tabletop 33 is hollow on the inside thereof. The supporting frame 34 is configured to support the tabletop 33 so as to be movable in the longitudinal directions of the tabletop 33. In the present example, the table 30 is an example of a medical table device.

The console 40 includes a memory 41, a display device 42, the input interface 43, and a processing circuit 44. Data communication among the memory 41, the display device 42, the input interface 43, and the processing circuit 44 is performed via a bus. Although the console 40 is described as a separate element from the gantry 10, the gantry 10 may include the console 40 or one or more of the constituent elements of the console 40.

For example, the memory 41 is realized by using a semiconductor memory element such as a Random Access Memory (RAM) or a flash memory, or a hard disk, an optical disk, or the like. For example, the memory 41 is configured to store therein the projection data and reconstruction image data. Further, for example, the memory 41 is configured to store therein imaging protocols corresponding to examined sites and purposes. In the following description, the imaging protocols may be referred to as scan plans. Further, the imaging protocols may simply be referred to as protocols. Further, for example, the memory 41 is configured to store therein various types of computer programs (hereinafter, "programs"). A storage area of the memory 41 may be provided in the X-ray CT apparatus 1 or may be provided in an external storage device connected via a network. In the present example, the memory 41 is an example of a storage unit.

The display device 42 is configured to display various types of information. The display device 42 is configured to output, for example, a medical image (a CT image) generated by the processing circuit 44, a Graphical User Interface (GUI) used for receiving various types of operations from an operator, and the like. The GUI used for receiving the various types of operations from the operator includes various types of operation screens related to an imaging protocol editing process. In the description below, the imaging protocol editing process may be referred to as a protocol editing process. As the display device 42, it is possible to use any of arbitrary various types of display devices, as appropriate. For example, as the display device 42, it is possible to use a Liquid Crystal Display (LCD) device, a Cathode Ray Tube (CRT) display device, an Organic Electroluminescence Display (OELD) device, or a plasma display device. In the present example, the display device 42 is an example of the display unit.

The display device 42 may be provided in any location in the control room. Further, the display device 42 may be provided for the gantry 10. Also, the display device 42 may be of a desktop type or may be structured by using a tablet terminal or the like capable of wirelessly communicating with the main body of the console 40. Furthermore, as the display device 42, one or more projectors may be used.

The input interface 43 is configured to receive various types of input operations from the operator, to convert the received input operations into electrical signals, and to output the electrical signals to the processing circuit 44. For example, the input interface 43 is configured to receive, from the operator, an acquisition condition used at the time of acquiring the projection data, a reconstruction condition used at the time of reconstructing a CT image, an image processing condition used at the time of generating a post-processing image from the CT image, and the like. For example, the input interface 43 is configured to receive various types of input operations from the operator performed on the various types of operation screens related to the protocol editing process. In the present example, the input interface 43 is an example of the input unit.

For example, as the input interface 43, it is possible to use a mouse, a keyboard, a trackball, a switch, a button, a joystick, a touchpad, a touch panel display device, and/or the like, as appropriate. In the present embodiments, the input interface 43 does not necessarily have to include the physical operation component parts as described above. For example, possible examples of the input interface 43 include an electrical signal processing circuit configured to receive an electrical signal corresponding to an input operation from an external input device provided separately from the apparatus and to output the electrical signal to the processing circuit 44. Further, the input interface 43 may be provided for the gantry 10. Alternatively, the input interface 43 may be configured by using a tablet terminal or the like capable of wirelessly communicating with the main body of the console 40.

The processing circuit 44 is configured to control operations of the entirety of the X-ray CT apparatus 1. The processing circuit 44 includes, as hardware resources thereof, a processor and memory elements such as a Read-Only Memory (ROM) and a RAM. By employing the processor configured to execute a program loaded into a memory, the processing circuit 44 is configured to execute, among others, a system controlling function 45, an image generating function 46, an image processing function 47, and a display controlling function 48. In the present example, the processing circuit 44 is an example of a processing unit.

By employing the system controlling function 45, the processing circuit 44 is configured to control various types of functions of the processing circuit 44 on the basis of input operations received from the operator via the input interface 43.

For example, the processing circuit 44 is configured to control generating, editing, and deleting any of pre-set imaging protocols and examination-purpose imaging protocols, on the basis of the input operations received from the operator via the input interface 43. For example, the processing circuit 44 is configured to control an imaging process performed on the patient P in accordance with a selected protocol displayed in a protocol display region on a scan executing screen (see FIG. 3, for example).

By employing the image generating function 46, the processing circuit 44 is configured to generate data by performing pre-processing processes such as a logarithmic conversion process, an offset correcting process, an inter-channel sensitivity correcting process, a beam hardening correction, and/or the like on the detection data output from the DAS 18. The processing circuit 44 is configured to store the generated data into the memory 41. The data (the detection data) prior to the pre-processing processes and the data after the pre-processing processes may collectively be referred to as projection data. The processing circuit 44 is configured to generate CT image data by performing a reconstruction process that implements a filter back-projection method, a successive approximation reconstruction method, machine learning, or the like, on the generated projection data (i.e., the projection data after the pre-processing processes). The processing circuit 44 is configured to store the generated CT image data into the memory 41.

By employing the image processing function 47, the processing circuit 44 is configured to convert the CT image data generated by the image generating function 46 into tomographic image data taken on an arbitrary cross-sectional plane or three-dimensional image data, by using a publicly-known method, on the basis of an input operation received from the operator via the input interface 43. For example, the processing circuit 44 may generate rendering image data in an arbitrary viewpoint direction, by performing a three-dimensional image processing process such as volume rendering, surface rendering, an image value projecting process, a Multi-Planar Reconstruction (MPR) process, a Curved MPR (CPR) process, or the like, on the CT image data. Alternatively, the three-dimensional image data such as the rendering image data in the arbitrary viewpoint direction may directly be generated by the image generating function 46. The processing circuit 44 is configured to store the tomographic image data or the three-dimensional image data into the memory 41.

Further, by employing the image processing function 47, the processing circuit 44 is configured to generate image data used for displaying various types of display screens related to an imaging protocol selecting process. In the explanations below, the imaging protocol selecting process may be referred to as a protocol selecting process.

By employing the display controlling function 48, the processing circuit 44 is configured to cause the display device 42 to display an image on the basis of any of various types of image data generated by the image processing function 47. Examples of the image displayed by the display device 42 include a CT image based on CT image data, a cross-sectional image based on cross-sectional image data taken on an arbitrary cross-sectional plane, and a rendering image in an arbitrary viewpoint direction based on rendering image data taken in an arbitrary viewpoint direction. Examples of the image displayed by the display device 42 include an image for displaying an operation screen and an image for displaying a notification and an alert for the operator. Examples of the operation screen include the various types of display screens related to the protocol selecting process. In the present example, the processing circuit 44 configured to realize the display controlling function 48 is an example of a display controlling unit.

The functions 45 to 48 do not necessarily have to be realized by the single processing circuit. It is also acceptable to structure the processing circuit 44 by combining together a plurality of independent processors, so that the functions 45 to 48 are realized as a result of the processors executing the programs. In this regard, the functions 45 to 48 may be realized as being distributed among or integrated into one or more processing circuits, as appropriate.

Although the console 40 was described as a single console configured to execute the plurality of functions, it is also acceptable to have the plurality of functions executed by separate consoles. For example, the functions of the processing circuit 44, such as the image generating function 46 and the image processing function 47, may be provided in a distributed manner.

Further, the processing circuit 44 does not necessarily have to be included in the console 40 and may be included in a consolidated server configured to collectively perform a process on pieces of detection data obtained by a plurality of medical image diagnosis apparatuses.

Further, post-processing processes may be performed by either the console 40 or an external workstation. Alternatively, both the console 40 and a workstation may perform the processes at the same time. As the workstation, it is possible to use, as appropriate, a computer including: a processor configured to realize the image generating function 46 and the image processing function 47; and memory elements such as a ROM and a RAM or the like as hardware resources thereof, for example.

Although not illustrated in FIG. 1, when the X-ray CT apparatus 1 performs an imaging process while injecting a contrast agent, an injecting device for the contrast agent is communicably connected to the processing circuit 44, so that the imaging process is performed while contrast agent injection timing of the injecting device is coordinated with imaging timing of the X-ray CT apparatus 1.

Further, to reconstruct X-ray CT image data, the reconstruction method may be either a full-scan reconstruction method or a half-scan reconstruction method. For example, according to the full-scan reconstruction method, by employing a reconstruction processing function 444, the processing circuit 44 uses projection data corresponding to a full circle around the patient P, i.e., 360 degrees. In contrast, according to the half-scan reconstruction method, the processing circuit 44 uses projection data corresponding to "180 degrees+a fan angle". In the present embodiments, for the sake of convenience in the explanation, it is assumed that the processing circuit 44 is configured to use the full-scan reconstruction method by which the reconstruction process is performed while using the projection data corresponding to a full circle around the patient P, i.e., 360 degrees.

The techniques of the present embodiments are applicable to the X-ray CT apparatus 1 of various types such as a third-generation CT or a fourth-generation CT. In this situation, the third-generation CT corresponds to a Rotate/Rotate type where an X-ray tube and a detector that are integrated together rotate around the patient. The fourth-generation CT corresponds to a Stationary/Rotate type where, while a large number of X-ray detecting elements arranged in a ring-shape array are fixed, only an X-ray tube rotates around the patient.

Further, besides single-tube X-ray computed tomography apparatuses, the techniques of the present embodiments are also applicable to so-called multi-tube X-ray computed tomography apparatuses in which a plurality of pairs each made up of an X-ray tube and a detector are installed on a rotating ring.

In the present embodiments, examples of the X-ray CT apparatus 1 having installed therein the integral-type X-ray detector 12 are explained; however, it is also possible to realize the techniques of the present embodiments as the X-ray CT apparatus 1 having installed therein a photon-counting-type X-ray detector.

Further, the X-ray CT apparatus 1 according to the present embodiments may be configured as a standing CT apparatus. In that situation, a supporting unit configured to support the patient P in a standing position instead of moving the tabletop 33 may be provided so as to be movable along the rotation axis of a rotating part of the gantry 10. In one example, a tabletop 33 or the table 30 do not necessarily have to be provided. Further, the X-ray CT apparatus 1 according to the present embodiments may be configured as a movable CT or a dental CT in which the gantry 10 and the table 30 are movable.

In the present embodiments, the X-ray CT apparatus 1 is used as the medical image diagnosis apparatus; however, possible embodiments are not limited to this example. The techniques of the present embodiments are also applicable to other medical image diagnosis apparatuses such as Magnetic Resonance Imaging (MRI) apparatuses, Positron Emission Tomography (PET) apparatuses, Single Photon Emission Computed Tomography (SPECT) apparatuses, X-ray diagnosis apparatuses, and ultrasound diagnosis apparatuses. In those situations, a controlling circuit in each of the medical image diagnosis apparatuses realizes the same functions as those realized by the processing circuit 44 of the present embodiments.

Further, the display control related to the protocol editing process according to the present embodiments do not necessarily have to be realized by the console 40 included in the X-ray CT apparatus 1 and may be realized by an external workstation, a PACS viewer, or a combination of the two.

Alternatively, it is also acceptable to provide the X-ray CT apparatus 1 with the gantry 10 and the table 30, so that a controlling device provided in common to a plurality of medical image diagnosis apparatuses in the hospital including the X-ray CT apparatus 1 is configured to realize a part of the aforementioned functions of the console 40. In that situation, for example, the console 40 includes the input interface 43 and the display device 42 configured to display screen displays from the controlling device or a GUI image. Inputs from the input interface 43 are sent to the controlling device via a communication network through a communication circuit (not illustrated) included in the console 40, so that the inputs are processed by the controlling device, and a GUI image updated in accordance with the inputs is output by a communication circuit of the controlling device and is received by the communication circuit of the console 40. In that situation, the GUI (explained later) is partially realized by the controlling device. Possible examples of function sharing between the console 40 and the controlling device are not limited to this example. It is also acceptable to configure the console 40 so as to update the GUI image in accordance with the inputs and to configure the controlling device so as to change and update image taking conditions, scan plans, and protocol information in accordance with the inputs or updates of the GUI image. These devices configured to realize the display control related to the protocol editing process according to the present embodiments are examples of the medical information display controlling device.

Next, the imaging protocol selecting process for an examination performed in an image diagnosis process using a medical image diagnosis apparatus such as the X-ray CT apparatus 1 according to the embodiment will be explained further in detail, with reference to the accompanying drawings.

For the image diagnosis process using a medical image diagnosis apparatus such as the X-ray CT apparatus 1, an operator (e.g., a responsible technologist or a radiologist) operating the medical image diagnosis apparatus carries out an examination by determining specifics of the examination on the basis of an examination order sent from a responsible medical doctor. In that situation, the operator may select an imaging protocol for the examination, from a list containing imaging protocols generated in advance. The imaging protocols in the list are generated in advance as generic imaging protocols for specific examinations on the basis of, for example, regulations in the hospital and/or a radiation dose guideline. In this situation, the imaging protocol includes, for example, a scan for a position determining purpose, a non-contrast-enhanced scan for each site, or a contrast-enhanced scan for each site. In other words, when X-ray CT image data is acquired on the basis of one imaging protocol, scans are performed in multiple sessions, so as to acquire X-ray CT image data corresponding to each of the scans.

When the list does not contain an optimal imaging protocol suitable for the examination order or the state of the patient, the operator may perform the imaging protocol optimization process, by reading an imaging protocol used as a base from the list and subsequently performing an operation to add a scan or to edit conditions, for example.

To perform the imaging protocol optimization process, after the imaging protocol is read, it is necessary to perform the operation of adding a scan or editing the conditions of the scans. In other words, the operator needs to edit image taking conditions so as to set the conditions suitable for the added scan and the existing scans. However, when the image taking conditions are changed, it is also necessary to optimize the reconstruction conditions as well. Accordingly, performing the imaging protocol optimization process would increase operations performed by the operator related to the imaging protocol editing process.

For example, in some situations, it may be possible to select an imaging protocol suitable for an examination by referring to the conditions of another imaging protocol or scans used in the past. However, when referring to the conditions of another imaging protocol or the scans used in the past, it is necessary to take the procedure where, while referring to those conditions, the operator sets appropriate conditions one by one. Accordingly, there is a demand for simplifying the operation steps of the operator related to the imaging protocol editing process.

Further, in some situations, it may be impossible to determine whether or not an imaging protocol is suitable for a certain examination, because it is not possible to understand the elements structuring the imaging protocol only from the name attached to the imaging protocol. In those situations, after editing the imaging protocol, the operator would need to perform an operation to cause the screen to transition to a display screen used for executing the scans. Until the conditions read and displayed on the display screen are checked, it would be difficult for the operator to determine whether or not the imaging protocol is suitable for the examination.

Further, in some situations, there may be a plurality of imaging protocols each including scans that are set with image taking conditions or reconstruction conditions of mutually the same system. These situations occur because each protocol is generated in accordance with a difference in the number of temporal phases during contrast-enhanced imaging processes or depending on whether or not subtraction is present. When there are two or more similar imaging protocols, managing the imaging protocols might require time and effort. Needless to say, it is possible to reduce the time and effort required in the management of the imaging protocols, by combining together two or more of the imaging protocols. However, as explained above, when imaging protocols are combined together (edited), it is necessary to set the conditions. For this reason, simply combining the imaging protocols would not be sufficient. Accordingly, there is a demand for further simplifying the operation steps performed by the operator.

As explained herein, when time and effort are required in selecting an imaging protocol suitable for an examination and managing the imaging protocols, the throughput of the image diagnosis process using the medical image diagnosis apparatus would be lowered. The present embodiments will provide, as explained below, a medical image diagnosis apparatus such as the X-ray CT apparatus 1 that is capable of reducing the operation steps of the operator related to selecting an imaging protocol suitable for an examination. Further, the present embodiments will provide a medical image diagnosis apparatus such as the X-ray CT apparatus 1 that is capable of reducing the time and effort related to managing the imaging protocols. In other words, the present embodiments will provide a medical image diagnosis apparatus such as the X-ray CT apparatus 1 that is capable of improving the throughput of the image diagnosis process.

The following will explain display screens displayed on a display device by the processing circuit 44, with reference to FIGS. 2 to 18. Each of the display screens is, for example, a screen used by a user to set conditions for an examination and the like and may be operated in accordance with inputs from the input interface 43. What is displayed on the screen corresponds to information about the examination. In accordance with operation inputs performed by the user, what is displayed on the screen is changed. In correspondence with the changes, settings are established by inputting, changing, adding, or deleting information as appropriate, with respect to the information about the examination.

Figure 2:
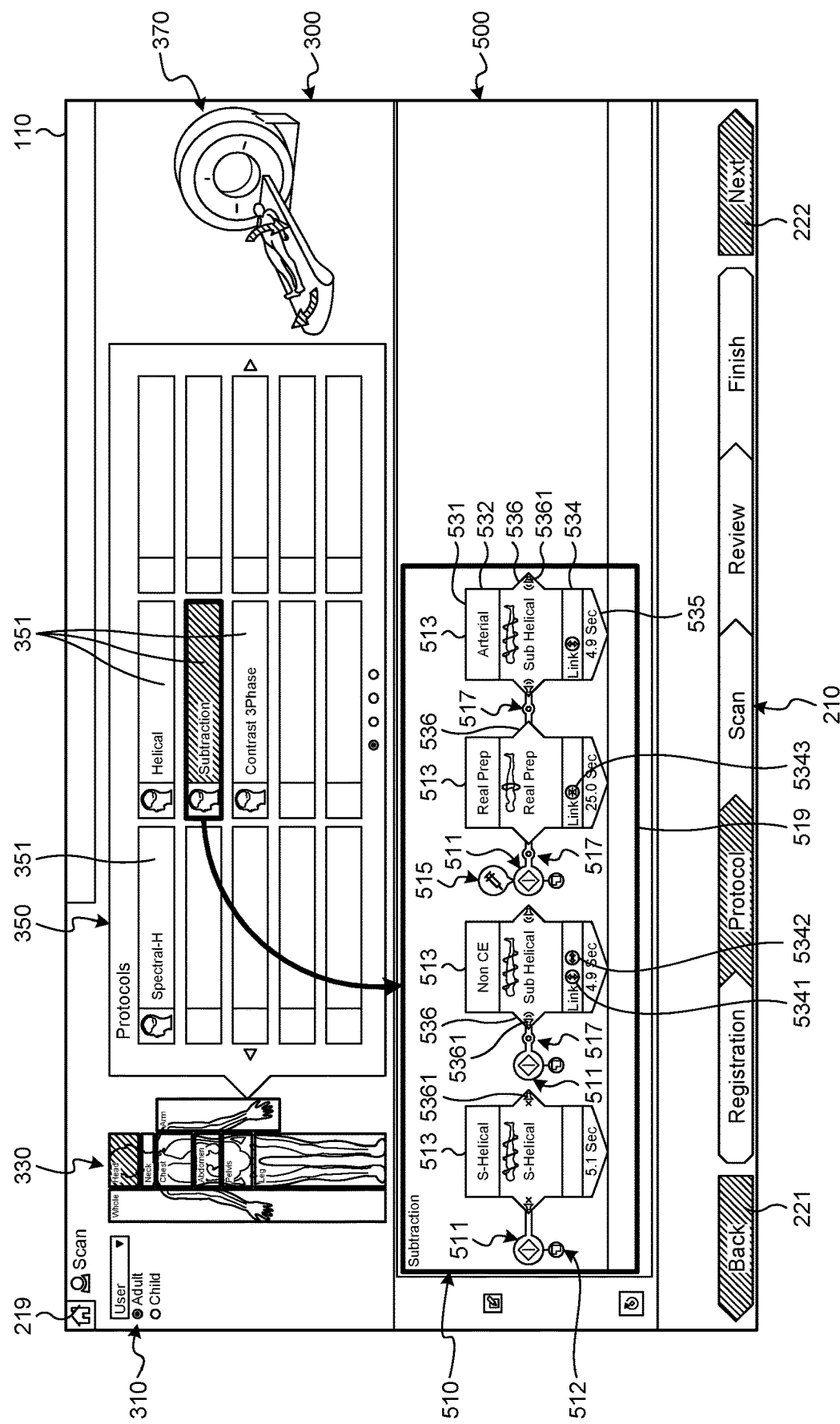
FIG. 2 is a drawing illustrating example (1) of a protocol selecting screen displayed by a display device according to the embodiment.

FIG. 2 is a drawing illustrating example (1) of a protocol selecting screen 110 displayed by the display device 42 according to the embodiment. The protocol selecting screen 110 is a screen used for selecting, editing, and adjusting a protocol to be used for an examination. The protocol selecting screen 110 may be referred to as a protocol editing screen or may be referred to as a protocol adjusting screen. Detailed conditions of the scans included in the protocol are primarily adjusted in the next phase, i.e., on a scan executing screen 130 (see FIG. 3, for example). In contrast, the protocol selecting screen 110 is primarily used for setting a flow in the entire protocol, such as a relationship between the scans, timing for pressing an emission switch, timing for injecting a contrast agent, and the like. Further, the protocol selecting screen 110 is also used for establishing settings related to progress of the scans such as the presence/absence and the content of audio guidance before and after each scan, as well as settings having a low possibility of being changed throughout the entire protocol such as patient positioning (e.g., head first or feet first). In this situation, the head-first patient positioning denotes positioning the patient so as to enter the gantry 10 head first. In contrast, the feet-first patient positioning denotes positioning the patient so as to enter the gantry 10 feet first. Further, because imaging protocols are primarily associated with sites of the patient's body, the protocol selecting screen 110 is also used for selecting a site to be imaged.

On the protocol selecting screen 110, the processing circuit 44 is configured to display a flow 210 of the examination. The flow 210 of the examination includes, for example, a plurality of phases, as illustrated in FIG. 2. For example, "Registration" denotes a phase in which the patient is registered. For example, "Protocol" denotes a phase in which a protocol is selected. For example, "Scan" denotes a phase in which a scan is executed. For example, "Review" denotes a phase in which images are reviewed. For example, "Finish" denotes a phase with an option to finish. In this situation, the processing circuit 44 is configured to display the flow 210 of the examination while placing an emphasis on a phase at the current point in time. For example, on the protocol selecting screen 110 in FIG. 2 used for the protocol selecting process, the processing circuit 44 is configured to display the section "Protocol" indicating the protocol selecting phase so as to be more emphasized compared to the other sections.

On the protocol selecting screen 110, for example, as illustrated in FIG. 2, the processing circuit 44 is configured to display a "Back" button 221 and a "Next" button 222 as buttons related to screen transitions. The "Back" button 221 instructs returning to an immediately preceding phase in the flow 210 of the examination. The "Next" button 222 instructs proceeding to an immediately following phase in the flow 210 of the examination.

On the protocol selecting screen 110, the processing circuit 44 is configured to display, as illustrated in FIG. 2, a protocol selecting region 300 (the first display region) and a protocol display region 500 (the second display region).

In the protocol selecting region 300, for example, the processing circuit 44 is configured to display, as illustrated in FIG. 2, an attribute selecting part 310 used for setting a patient attribute such as "Adult" or "Child". Further, for example, the processing circuit 44 is configured to display, as illustrated in FIG. 2, a site selecting part 330 used for setting an examined site such as "Whole", "Head", "Neck", "Chest", "Abdomen", "Pelvis", "Leg", or "Arm". In this situation, the processing circuit 44 is configured to display the patient attribute and the examined site that were selected, in an emphasized manner. Further, for example, the processing circuit 44 is configured to display, as illustrated in FIG. 2, a patient positioning icon 370 indicating position information of the patient P. The patient positioning icon 370 is an icon used for establishing a setting of patient positioning for the patient. The operator is able to set one of the head-first positioning and the feet-first positioning, by selecting the patient positioning icon 370.

In the protocol selecting region 300, the processing circuit 44 is configured to display, in a list display region 350, a list of a plurality of imaging protocols that are applicable to the site selected in the site selecting part 330. In the following description, the list of imaging protocols may simply be referred to as a protocol list. In the list display region 350, for example, the processing circuit 44 is configured to display, as illustrated in FIG. 2, icons 351 respectively corresponding to one or more imaging protocols that are valid on the patient attribute and the examined site that were set. An icon 351 "Spectral-H" represents a protocol for performing a helical imaging process by using dual-energy CT or photon-counting multi-energy CT. Another icon 351 "Helical" represents a protocol for performing a normal helical CT scan. Yet another icon 351 "Subtraction" represents a protocol for obtaining a difference image between images acquired in two scans performed before and after injecting a contrast agent. Yet another icon 351 "Contrast 3Phase" represents an arterial phase, a portal vein phase, and an equilibrium phase. For the sake of convenience in the explanation, the display of the imaging protocols by way of displaying the icons 351 may simply be referred to as "imaging protocols" in the following description. Further, the imaging protocols serving as imaging information and corresponding to the icons 351 may be referred to as the icons 351.

In the protocol display region 500, the processing circuit 44 is configured to display an icon 510 indicating detailed information of the selected imaging protocol. In the following description, the selected imaging protocol may simply be referred to as a selected protocol. In other words, the icon 510 representing the selected protocol indicates the detailed information of the imaging protocol selected by the operator from the protocol list displayed in the list display region 350. As the icon 510 representing the detailed information of the selected protocol, the processing circuit 44 is configured to display pieces of information representing elements structuring the imaging protocol such as operations to be performed by the operator and the scans included in the selected protocol, so as to be arranged in a time series (in the sequential order of execution) from the left side to the right side of the screen, as illustrated in FIG. 2 for example.

For example, as illustrated in FIG. 2, with respect to the imaging protocol represented by the icon 351 "Subtraction", the processing circuit 44 is configured to display, as information indicating the operations to be performed by the operator, a radiation emission icon 511 representing an operation to turn on a radiation emission switch and an icon 515 representing the injection of a contrast agent. Underneath the radiation emission icon 511, a start mode icon 512 used for setting a start mode is displayed. Setting the start mode denotes setting a location in which the radiation emission switch can be pressed when starting a scan. As the location where the radiation emission switch can be pressed, it is possible to select an option from among "control pad", "gantry", and "hand switch".

Further, as illustrated in FIG. 2, for example, the processing circuit 44 is configured to display, as information indicating the scans included in the selected protocol, scan icons 513 representing the following imaging processes that are included in the imaging protocol represented by the icon 351 "Subtraction": "S-Helical", "Non CE", "Real Prep (CT fluoroscopy to monitor the contrast agent)", and "Aterial (imaging in the arterial phase)". As explained herein, each of the imaging protocols includes at least one scan.

Each of the scan icons 513 displays information about the corresponding scan, in a certain format using text or image information. For example, in FIG. 2, within each of the frames 531 that are substantially rectangular, the name of the scan is displayed in an upper region 532, whereas the type of the scan is displayed by using text and an icon in a region 533 underneath near the center. As different types of scans displayed in a region 5133 using text and icons, FIG. 2 illustrates "S-Helical (helical imaging for a position determining imaging process or a scanogram taking process)", "Sub-Helical (helical imaging for subtraction)", and "Reap-Prep". In a region 534 underneath, text "Link" indicating a setting to synchronize conditions between scans and icons indicating the types of the conditions to be synchronized are displayed. For example, in the scan icon 513 of "Non-CE", an icon 5341 indicating that imaged ranges in the Z-direction are to be coordinated and another icon 5342 indicating that the sizes (the Fields of View [FOVs]) of the imaged ranges are to be coordinated are displayed. Because "S-Helical" denotes scanograms, "Link" is not displayed, and the settings are configured so that the image taking conditions will not be coordinated. Within the frame of the "Arterial" scan, "Link" is displayed, which means a setting is established so that the image taking conditions are to be coordinated. Also, an icon 5341 is displayed so as to indicate that the imaged ranges in the Z-direction can be coordinated. For the "Real Prep" scan, next to the display of "Link", an icon 5343 is displayed so as to indicate a mode in which the subsequent scan (the "Arterial" scan in the present example) is executed under a specific condition so as to be started as soon as the Prep is finished.

Further, in the very bottom region 535, a time period required by each of the scans is displayed.

The left side and the right side of the substantially-rectangular frame 531 each have a triangular protrusion 536 where a speaker icon 5361 is displayed so that the presence/absence of announcement audio at the start of the scan (the left side) and at the end of the scan (the right side) is indicated depending on the type of the icon 5361.

Further, for example, the processing circuit 44 is configured to display, as illustrated in FIG. 2, joint icons 517 between certain elements to be executed successively among the elements included in the icon 510 of the selected protocol. Further, the processing circuit 44 is also configured to display an icon 519 indicating a range of the pertinent selected protocol. FIG. 2 illustrates an example of a rectangular frame serving as the icon 519. The icon 519 indicating the range of the selected protocol does not necessarily have to be displayed.

In an example, on the protocol selecting screen 110, from among the plurality of imaging protocol icons 351 displayed in the list display region 350, the operator is able to cause one of the imaging protocol icons 351 (the first imaging protocol) representing the imaging protocol which he/she wishes to select, to be displayed in the protocol display region 500, by performing a drag & drop operation (the first operation input). The drag & drop operation may be realized as an operation using a mouse or may be realized as an operation using a touch panel.

In this situation, on the basis of the input operation received from the operator via the input interface 43, the processing circuit 44 displays the icon 351 representing the imaging protocol selected in the protocol selecting region 300 so as to be more emphasized than the other sections, as a display indicating an active state. Further, in the protocol display region 500, the processing circuit 44 displays the imaging protocol represented by the selected icon 351 as the icon 510 of the selected protocol.

In this situation, the operation performed by the operator to select the icon 351 of the arbitrary imaging protocol from the protocol selecting region 300 and to cause the selected icon to be displayed in the protocol display region 500 does not necessarily have to be the drag & drop operation and may be realized by other operation methods (the first operation input). In one example, on the protocol selecting screen 110, the operator may single click on the icon 351 representing the imaging protocol which he/she wishes to select from the list display region 350 displayed in the protocol selecting region 300. After that, while the icon 351 representing the imaging protocol which he/she wishes to select is displayed in the emphasized manner, the operator may single click on the protocol display region 500. In that situation, on the basis of the input operation received from the operator via the input interface 43, the processing circuit 44 brings the display of the icon 351 of the imaging protocol that was single clicked in the protocol selecting region 300 into the active state (emphasized display). Further, when the protocol display region 500 is clicked on, the processing circuit 44 causes detailed information of the icon 351 representing the imaging protocol in the active state, i.e., the icon 510 of the selected protocol, to be displayed in the protocol display region 500 which was clicked on.

The scan icons 513, the radiation emission icons 511, the start mode icon 512, the joint icons 517, and the various types of icons displayed within the frames of the scan icons 513 described above can be changed in accordance with operation inputs performed by the user on the icons. In accordance with the operation inputs, various types of conditions related to the protocols may be changed. For example, in response to a click on the joint icon 517 for "Real-Prep", a display is realized in which the "Real-Prep" scan and the "Non-CE" scan can be joined together (which is a display similar to the joint display between "Real-Prep" and "Arterial"). In response to the radiation emission switch being pressed at the start of the Non-CE, the joined scans can automatically be executed, as appropriate. The timing with which the latter scan of the two joined scans is started may be set as an elapsed time period since a preceding event. For example, the start timing of the latter scan is set, by setting an elapsed time period since the time when the emission switch is pressed, when the "Non-CE" scan is started or ended, or the like. This setting can also be established in accordance with an operation input performed by the user on the protocol display region 500.

As for various types of conditions related to the contrast agent, it is possible to establish settings on the protocol selecting screen 110 or the scan executing screen 130 (see FIG. 3, for example), and it is also possible to establish settings from the contrast agent injection device (not illustrated). It is possible to determine, in advance, which condition is to be used in the situation where a condition set from the injection device is different from a condition set on the X-ray CT apparatus 1, i.e., when the conditions are in conflict with each other. In other words, the processing circuit 44 judges whether the condition on the X-ray CT apparatus 1 is to be used or the condition from the injection device is to be used, by referring to setting information stored in the memory 41 of the X-ray CT apparatus 1. When the condition on the X-ray CT apparatus 1 is to be used, the condition is transmitted to the injection device. On the contrary, when the condition from the injection device is to be used, the condition set from the injection device is obtained from the injection device, and also, the condition set in the X-ray CT apparatus 1 is loaded, so as to judge whether or not the two conditions match each other. When the conditions do not match, a message indicating the discrepancy may be displayed on the screen in a predetermined position of the display device 42. Further, the condition obtained from the injection device is configured into the X-ray CT apparatus 1 so as to be displayed in the protocol display region 500 on the protocol selecting screen 110 or the scan executing screen 130 so as to reflect the information. With this arrangement, it is possible to avoid the conflict between the conditions. Further, because it is possible to set, in advance, which condition is to be used, it is possible to reduce the time and effort required by the condition setting process.

Figure 3:
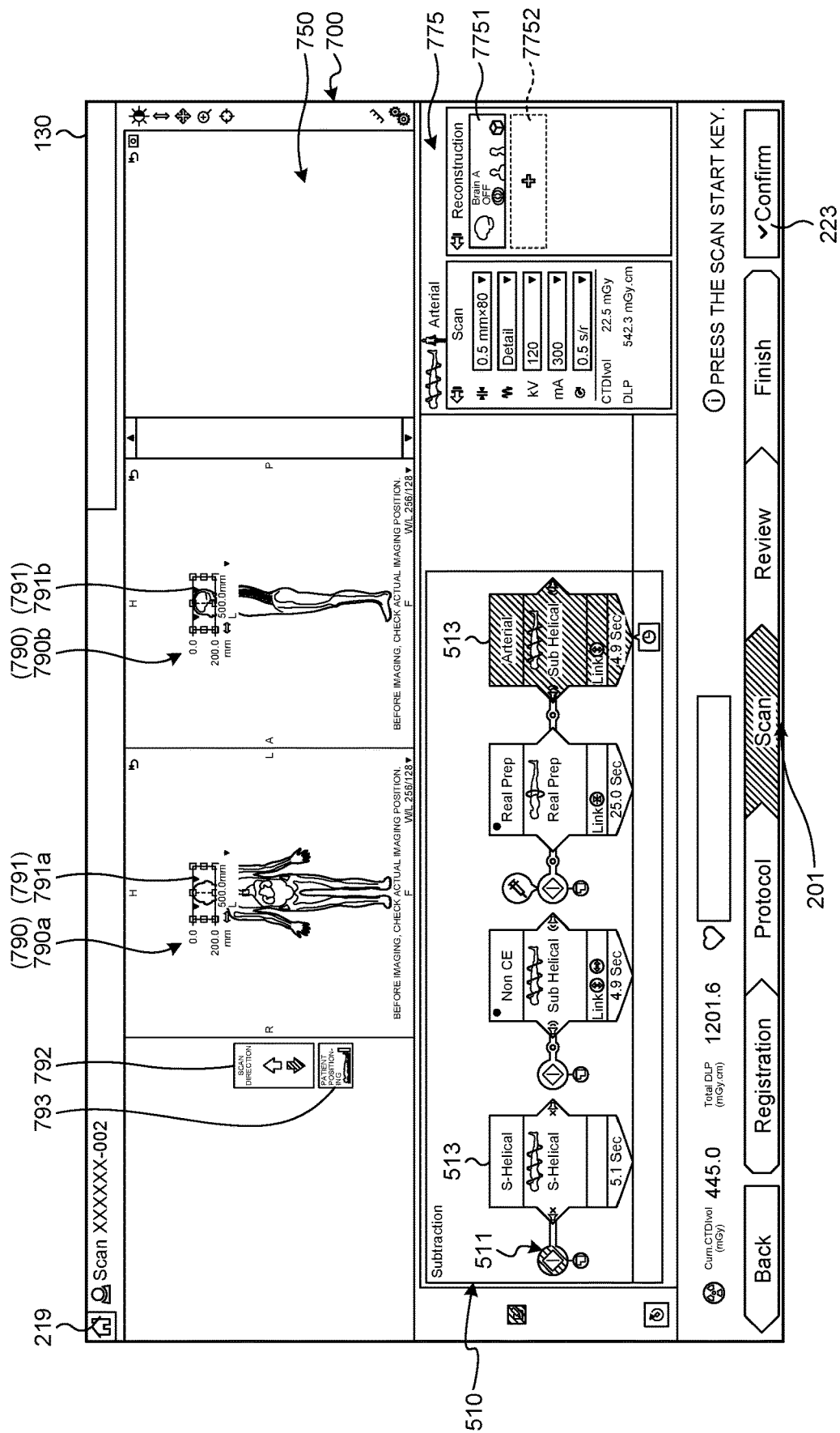
FIG. 3 is a drawing illustrating example (1) of a scan executing screen displayed by the display device according to the embodiment.

FIG. 3 is a drawing illustrating example (1) of the scan executing screen 130 displayed by the display device 42 according to the embodiment.

On the scan executing screen 130, the processing circuit 44 is configured to display, as illustrated in FIG. 3, the protocol display region 500 that was used for setting the protocol on the protocol selecting screen 110, which was the display screen in the protocol selecting phase that preceded. Further, the processing circuit 44 is configured to further display a scan information display region 700 including an imaging information display region 750 and a detailed condition display region 775. Further, for example, on the scan executing screen 130 in FIG. 3 used for executing the scan, the processing circuit 44 is configured to display the section "Scan" representing the scan execution phase in the flow 210 of the examination, so as to be more emphasized than the other sections. On the scan executing screen 130, the already-edited protocols are displayed, and also, detailed conditions of a certain scan designated from the protocol are displayed. In addition, it is also possible to check images obtained from the scan.

In the imaging information display region 750, the processing circuit 44 is configured to cause information to be displayed such as information indicating scan ranges 791 (791*a* and 791*b*) over a human body image 790 of a human body model or the patient's image, information 792 indicating a scan direction, and information 793 about patient positioning. Further, in the detailed condition display region 775, the processing circuit 44 is configured to cause various types of information related to the scan to be displayed, such as information about scan conditions and information about reconstruction conditions. In the scan information display region 700, an image obtained from the scanogram imaging (the position determining imaging) is displayed, so that it is possible to set a scan range. Further, during the scan and after the scan, an image obtained from the scan is displayed, so that the user is able to check the images.

In one example, on the protocol selecting screen 110 illustrated in FIG. 2, by selecting the "Next" button 222, the operator is able to cause the screen to transition to the scan executing screen 130 as illustrated in FIG. 3, while keeping the display of the protocol display region 500 illustrated in FIG. 2. In this situation, on the basis of the operation (a third operation input) performed on the "Next" button 222 received from the operator via the input interface 43, the processing circuit 44 reads the information such as the scan conditions to be displayed in the scan information display region 700. After that, the processing circuit 44 displays the scan executing screen 130 and makes a screen transition from the protocol selecting screen 110.

As explained herein, by performing an operation such as the drag & drop operation (the first operation input), the operator operates on the icon 351 representing the imaging protocol which he/she wishes to select from the list display region 350. As a result, the operator is able to cause the detailed information of the selected imaging protocol, i.e., the icon 510, to be displayed in the protocol display region 500. Further, by causing the icon 510 corresponding to the selected imaging protocol to be displayed in the protocol display region 500, the operator is able to easily check the scans and the like included in each imaging protocol. Consequently, even when the operator is unable to determine from the name alone whether an imaging protocol is suitable for the examination, the operator is able to easily determine the suitability without the need to make a screen transition to the scan executing screen 130.

Further, while the elements structuring the imaging protocol selected on the protocol selecting screen 110 remain displayed in the protocol display region 500, the operator is able to check, on the scan executing screen 130, detailed parameter information to be used at the time of acquiring X-ray CT image data. Consequently, on the scan executing screen 130 also, the operator is able to easily understand the flow in the examination, a state at the current point in time, an operation to be performed next, and the like by referring to the protocol display region 500. Further, the operator is able to execute the one or more scans as one imaging protocol, in the sequential order corresponding to the scan icons 513 representing the one or more scans and being displayed in the protocol display region 500.

Further, what is displayed in the protocol display region 500 on the scan executing screen 130 does not necessarily have to be exactly the same as what is displayed in the protocol display region 500 on the protocol selecting screen 110. In other words, identicality between the protocol display regions 500 on the two screens is sufficient when the two are substantially identical. One of the reasons is that the sizes of the display regions cannot be exactly the same in some situations, because the scan executing screen 130 has other display regions to be displayed, and the protocol selecting screen 110 also has other display regions.

In those situations, the protocol display region 500 on the scan executing screen 130 may display a reduced-size version of the protocol display presented in the protocol display region 500 on the protocol selecting screen 110. In particular, when the screen configurations illustrated in FIGS. 2 and 3 are used, because the protocol display region 500 on the scan executing screen 130 is smaller, reducing the size makes it possible to display the whole image in an easy-to-understand manner. Alternatively, in order to display each of the scans in an easier-to-understand manner, it is also acceptable to realize the display in enlargement. Whether on the protocol selecting screen 110 or on the scan executing screen 130, the protocol display region 500 is able to sequentially display pieces of information about the protocol, in response to a transverse scroll operation. Alternatively, in place of or in combination with the enlarged/reduced display, it is also acceptable to cause a part of the information not to be displayed or to cause more information to be displayed. In another example, it is also acceptable to keep the protocol display region 500 in a non-display state, while no operation input is provided. In response to a specific input, (e.g., when a mouse cursor is positioned in a region 201 near the bottom center of the display device), the protocol display region 500 may be displayed together with an animation to slide in from the bottom of the screen. Furthermore, in response to another specific operation (e.g., when the mouse curser moves away from the protocol display region 500 displayed), the protocol display region 500 may be brought into a non-display state together with an animation to slide out toward the bottom center. When such a pop-up display scheme is adopted, for example, a certain part of the display in the protocol display region (e.g., only the scan currently executed) may be constantly displayed on the scan executing screen 130. By using the pop-up display scheme described herein, it is possible to efficiently display the necessary information in the limited display region and to thus contribute to making the workflow more efficient.

As explained above, certain slight changes are permitted in relation to the display modes on the screens, namely, the protocol selecting screen 110 and the scan executing screen 130. As for the screens, it is sufficient when the scan executing screen 130 displays certain information which the user himself/herself edited on the protocol selecting screen 110 and which he/she is able to recognize as what was displayed on the protocol selecting screen 110.

Next, a function to adjust the scan ranges 791 according to an aspect of the embodiment will be explained. For example, let us discuss a situation in which, when the input interface 43 includes a mouse, the scan ranges are adjusted by using the mouse. As the human body image 790 including a front-view image 790a and a lateral-view image 790b, a human body model may be used before the scanogram is taken, whereas a patient's image obtained from the scanogram may be used after the scanogram is taken. When helical imaging or a conventional scan (a volume scan) not involving the moving of the table 30 is performed to take the scanogram, the processing circuit 44 may generate front-view image data and lateral-view image data from three-dimensional images obtained from the scan so as to cause the display device 42 to display the front-view image 790a and the lateral-view image 790b.

In FIG. 3, to adjust the sizes of the scan ranges 791a and 791b, adjustments on the front-view image 790a can be made primarily in the Z-direction and the X-direction, whereas adjustments on the lateral-view image 790b can be made primarily in the Z-direction and the Y-direction. Further, when the position of an imaged region is to be adjusted, it is convenient to arrange a frame indicating the imaged region so as to be movable in arbitrary directions. For the duration in which a first button operation (e.g., a right click) is performed on the mouse while the frame indicating the imaged region is in a selected state, the processing circuit 44 moves the frame in an arbitrary direction in accordance with the moving direction of the mouse. In contrast, for the duration in which a second button operation (e.g., a left click) is performed on the mouse, the processing circuit 44 exercises display control so that the frame can be moved only in up-and-down directions or left-and-right directions on the screen. The control is exercised by extracting a component in the up-and-down directions or a component in the left-and-right directions from the moving directions of the mouse, so as to move the frame in accordance with the extracted component.

The selection from between the up-and-down directions and the left-and-right directions shall be made by selecting the directions in which the first move in an amount equal to or larger than a prescribed level is made after the second button operation is started, for example. For example, in response to the second button operation, displacements in the up-and-down directions and displacements in the left-and-right directions are separately accumulated during the button operation, so as to select, as the moving directions, the directions of which the accumulated amount first exceeds the predetermined threshold value. When the up-and-down directions are selected, the moving of the frame in response to the mouse may be restricted (e.g., prohibited from being moved) during the accumulation time period. When the first moving direction (e.g., the up-and-down directions) is selected, the processing circuit 44 is configured to move the frame in the first moving direction in accordance with the operation direction of the mouse, while restricting the moving of the frame in the second moving direction (the left-and-right directions). When the second moving direction is selected, the processing circuit 44 is configured to move the frame in the second moving direction in accordance with the operation direction of the mouse, while restricting the moving of the frame in the first moving direction. In response to an end of the second button operation, the processing circuit 44 is configured to cancel the restriction on the moving direction. By exercising control in this manner, it is possible to adjust the scan ranges 791a and 791b more efficiently.

Figure 4:
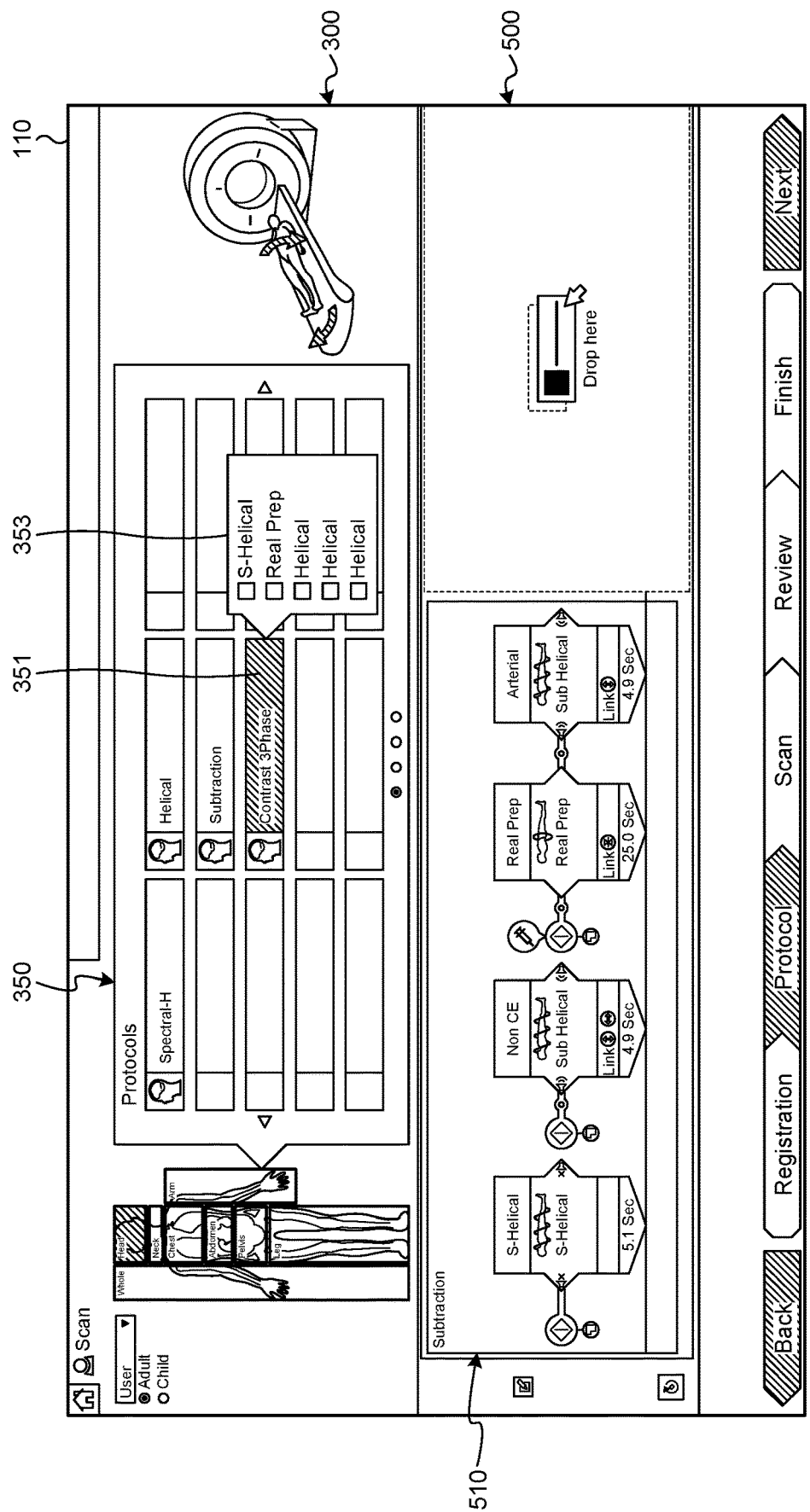
FIG. 4 is a drawing illustrating example (2) of the protocol selecting screen displayed by the display device according to the embodiment.

FIG. 4 is a drawing illustrating example (2) of the protocol selecting screen 110 displayed by the display device 42 according to the embodiment.

With reference to FIG. 2, the example was explained in which, by performing the drag & drop operation or the like to cause the icon 510 representing the selected protocol to be displayed, it is possible to check the content of the imaging protocol on the protocol selecting screen 110 in the same manner as on the scan executing screen 130; however, possible embodiments are not limited to this example. It is also acceptable to cause the content of the imaging protocol represented by the icon 351 to be displayed by realizing a display in the following manner.

In the protocol selecting region 300, the processing circuit 44 may be configured to display a scan list 353. The scan list 353 indicates the scans included in the imaging protocol selected by the operator from the list display region 350. For example, as illustrated in FIG. 2, the processing circuit 44 displays, as the scan list 353, icons representing the scans included in the imaging protocol represented by the icon 351 "Contrast 3Phase". In the example in FIG. 2, the scan list 353 contains the icons representing the scans "S-Helical", "Real Prep", "Helical", "Helical", and "Helical".

In one example, while the icon 351 representing the imaging protocol which the operator wishes to select is displayed in an emphasized manner, the operator again performs a single click (a fourth operation input) on the icon 351 of the imaging protocol displayed in the emphasized manner. In this situation, on the basis of the input operation (the fourth operation input) received from the operator via the input interface 43, the processing circuit 44 causes the scan list 353 of the imaging protocol represented by the clicked icon 351 in the active state to be displayed in a pop-out display. Further, similarly to the operation (the first operation input) performed on any of the icons 351 in the list display region 350, the operator is able to select any of the scans included in the imaging protocol represented by the icon 351, i.e., any of the scans in the scan list 353. The same applies to the processes performed by the processing circuit 44.

As for the pop-up display of the scan list 353, only the scan names may be displayed as illustrated in FIG. 4. Alternatively, it is also acceptable to use the same display format as the display format used in the protocol display region 500 in FIGS. 2 and 3.

As explained above, by performing a single click twice on the icon 351 representing the imaging protocol which the operator wishes to check from the list display region 350, the operator is able to cause the scan list 353 to be displayed in the pop-up display and to perform the simple checking process by using the pop-up display.

Figure 5:
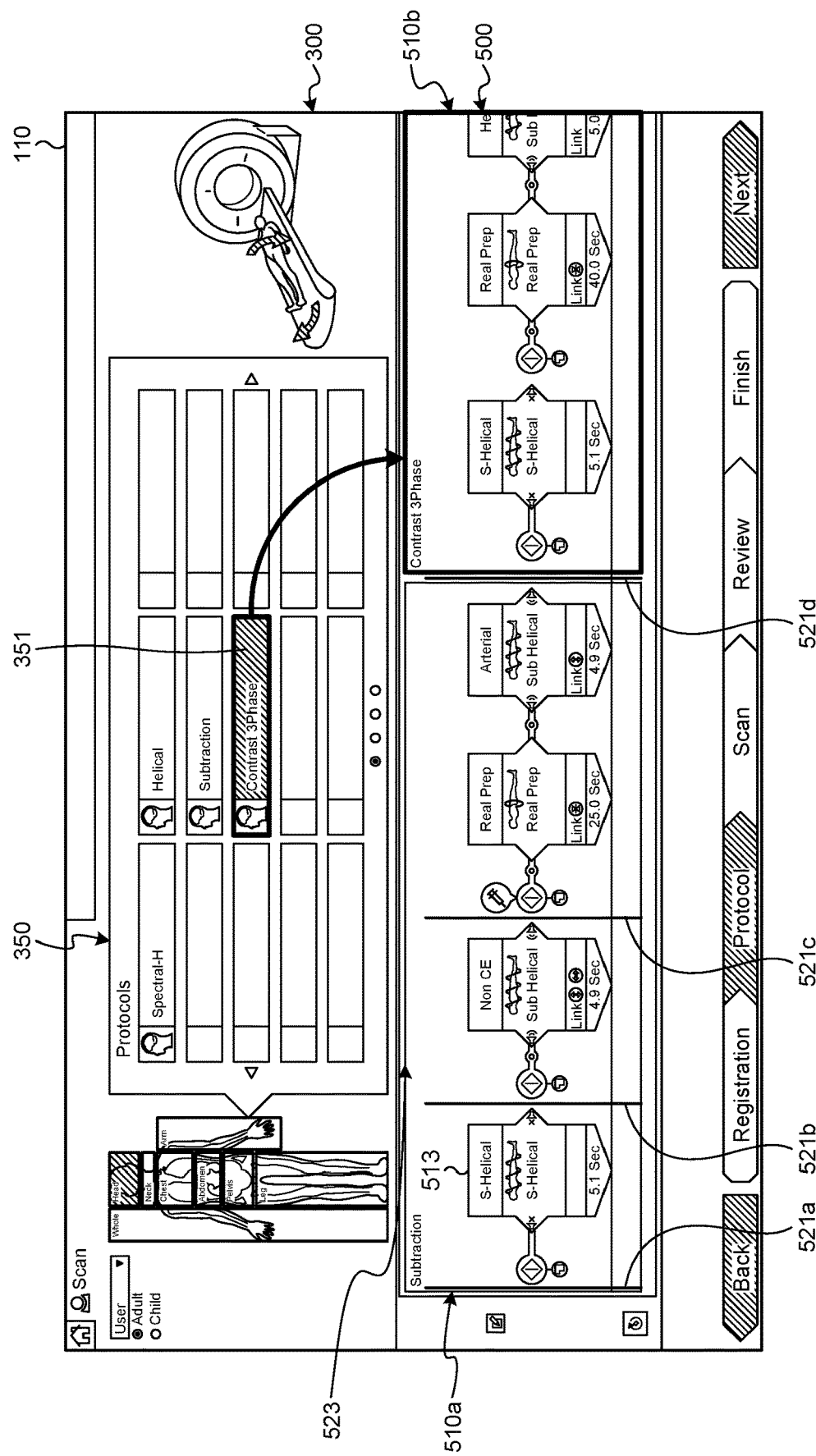
FIG. 5 is a drawing illustrating example (3) of the protocol selecting screen displayed by the display device according to the embodiment.

FIG. 5 is a drawing illustrating example (3) of the protocol selecting screen 110 displayed by the display device 42 according to the embodiment.

The example was explained in which, by performing the drag & drop operation or the like, the detailed information of the imaging protocol is displayed when the icon 351 representing the protocol is selected. In addition, while in the display state, it is also possible to perform an operation (the second operation input) to add, insert, replace, or delete another imaging protocol. In the following sections, with reference to FIG. 5, an example will be explained in which, on the protocol selecting screen 110 in FIG. 2, the icon 351 (the second imaging protocol) representing the imaging protocol "Contrast 3Phase" is further selected.

In one example, the operator performs a drag & drop operation on the icon 351 representing the imaging protocol "Contrast 3Phase" which he/she wishes to select, so as to be dropped in the protocol display region 500. Upon detection of the start of the drag & drop operation on the icon 351 on the basis of the input operation received from the operator via the input interface 43, the processing circuit 44 is configured to display, in the protocol display region 500, icons 521 (521*a* to 521*d*) indicating positions in which an icon 510 representing detailed information of the imaging protocol can be inserted. FIG. 5 illustrates solid lines as the icons 521. With this arrangement, when starting the drag & drop operation, the operator is able to easily understand the positions in which the icon 510 corresponding to the imaging protocol "Contrast 3Phase" can be inserted.

For example, the operator may drop the icon 351 of the imaging protocol "Contrast 3Phase" in an area in the latter part of the protocol display region 500 (in the position of the icon 521*d* and the right side thereof in FIG. 5). In this situation, as illustrated in FIG. 5, the processing circuit 44 causes an icon 510*b* of "Contrast 3Phase" to be additionally displayed to the rear (the tail end) of the icon 510*a* of "Subtraction".

For example, the operator may drop the icon 351 of the imaging protocol "Contrast 3Phase" in an area at the head of the protocol display region 500 (in the position of the icon 521*a* in FIG. 5). In this situation, the processing circuit 44 causes the icon 510*b* of "Contrast 3Phase" to be additionally displayed at the head of the icon 510 of the selected protocol currently displayed, i.e., to the front of the icon 510*a* of "Subtraction".

For example, the operator may display the icon 351 of the imaging protocol "Contrast 3Phase" between the scan icons 513 (in the position of the icon 521*b* or 521*c* in FIG. 5) included in the icon 510*a* of "Subtraction" displayed in the protocol display region 500. In this situation, the processing circuit 44 causes the icon 510*b* of "Contrast 3Phase" to be additionally displayed between those scan icons 513 in the icon 510*a* of "Subtraction".

In another example, the operator may drop the icon 351 of "Contrast 3Phase" in a space 523 in the upper part of the protocol display region 500. In this situation, the processing circuit 44 replaces the icon 510*a* of "Subtraction" currently displayed, with the icon 510*b* of "Contrast 3Phase".

In yet another example, the operator may drop the icon 510*a* of "Subtraction" currently displayed in the protocol display region 500, into an end part of the protocol selecting screen 110 or the list display region 350. In this situation, the processing circuit 44 deletes the icon 510*a* of "Subtraction" currently displayed from the protocol display region 500. Further, the processing circuit 44 may also separately display, on the protocol selecting screen 110, an icon indicating a drop destination used for deleting the icon 510 of the selected protocol from the protocol display region 500.

In yet another example, when a plurality of imaging protocols are combined together, the operator is also able to rearrange, in the protocol display region 500, the icons 510 (the icons 510*a* and 510*b* in FIG. 5) of the selected protocol currently displayed, by performing a drag & drop operation, in units of protocols. In this situation, as explained above, upon detection of the start of the drag & drop operation on the icon 510 in the protocol display region 500 on the basis of the input operation received from the operator via the input interface 43, the processing circuit 44 causes the icons 521 (521*a* to 521*d*) to be displayed in the protocol display region 500 so as to indicate the positions in which the icon 510 corresponding to the imaging protocol can be inserted.

The example was explained in which, upon detection of the start of the drag & drop operation, the icons 521 (521*a* to 521*d*) are displayed in the protocol display region 500 so as to indicate the positions where the icon 510 corresponding to the imaging protocol can be inserted; however, possible embodiments are not limited to this example.

For example, when the icon 351 of the imaging protocol is made closer, by a drag operation, to a destination position within the protocol display region 500, the processing circuit 44 may indicate, to the operator, that insertion or addition into those positions is possible by displaying the icons 521.

Further, for example, in place of the icons 521, the processing circuit 44 may also display an animation corresponding to the drag operation. In one example, when the icon 351 of the imaging protocol is made closer, by a drag operation, to a destination position within the protocol display region 500, the processing circuit 44 may cause the icons 510 positioned adjacent to an insertable position to be displayed with a wider interval therebetween. In this situation, the processing circuit 44 does not change the intervals in the positions where insertion and addition are not possible.

Further, upon detection of the start of a drag & drop operation, the processing circuit 44 may also display, in an emphasized manner, one of the icons 510 that is replaceable among the icons 510 currently displayed. In one example, the processing circuit 44 may cause the replaceable icon 510 to be displayed in a highlighted manner or with a border depicting the outline.

Further, not only upon detection of the start of a drag & drop operation, the processing circuit 44 may cause the replaceable icon 510 of the selected protocol to be displayed in an emphasized manner also when the icon 351 of the imaging protocol is made closer, by a drag operation, to the destination position within the protocol display region 500.

Further, in response to an operation input by the operator, the processing circuit 44 may be configured to cancel the display of the icon 519 indicating the inside of the icon 510 of the selected protocol, to make it possible to insert the icon 510 of another imaging protocol between the scan icons 513 within the icon 510 of the selected protocol.

As explained above, by performing the drag & drop operation or the like, the operator is able to easily edit the icon 510 of the selected protocol in the protocol display region 500. In other words, it is possible to reduce the operation steps of the operator related to the protocol editing process.

With reference to FIG. 5, the examples were explained in which the protocol is edited in units of protocols, by adding or inserting the imaging protocol into the protocol display region 500 or replacing, moving (rearranging) or deleting the selected protocol currently displayed; however, possible embodiments are not limited to these example. For instance, in the protocol display region 500, it is also possible to add or insert any of the scans included in the imaging protocols in units of scans, by performing a drag & drop operation or the like. Similarly, as for the icons of the scans included in the icons 510 (510*a* and 510*b*) currently displayed in the protocol display region 500, it is also possible to replace, move (rearrange), or delete any of the icons in units of scans. By using this mode, it is also possible to achieve the same advantageous effects as described above.

Further, in response to an operation input performed by the operator, in the intervals between the scan icons 513, the processing circuit 44 may cancel any of the joints between the scans that are scheduled to be executed successively as indicated by the joint icons 517 in FIG. 2, for example. In that situation, the operator is able to make an insertion in the positions of the joint icons 517, either in units of protocols or in units of scans.

Figure 6:
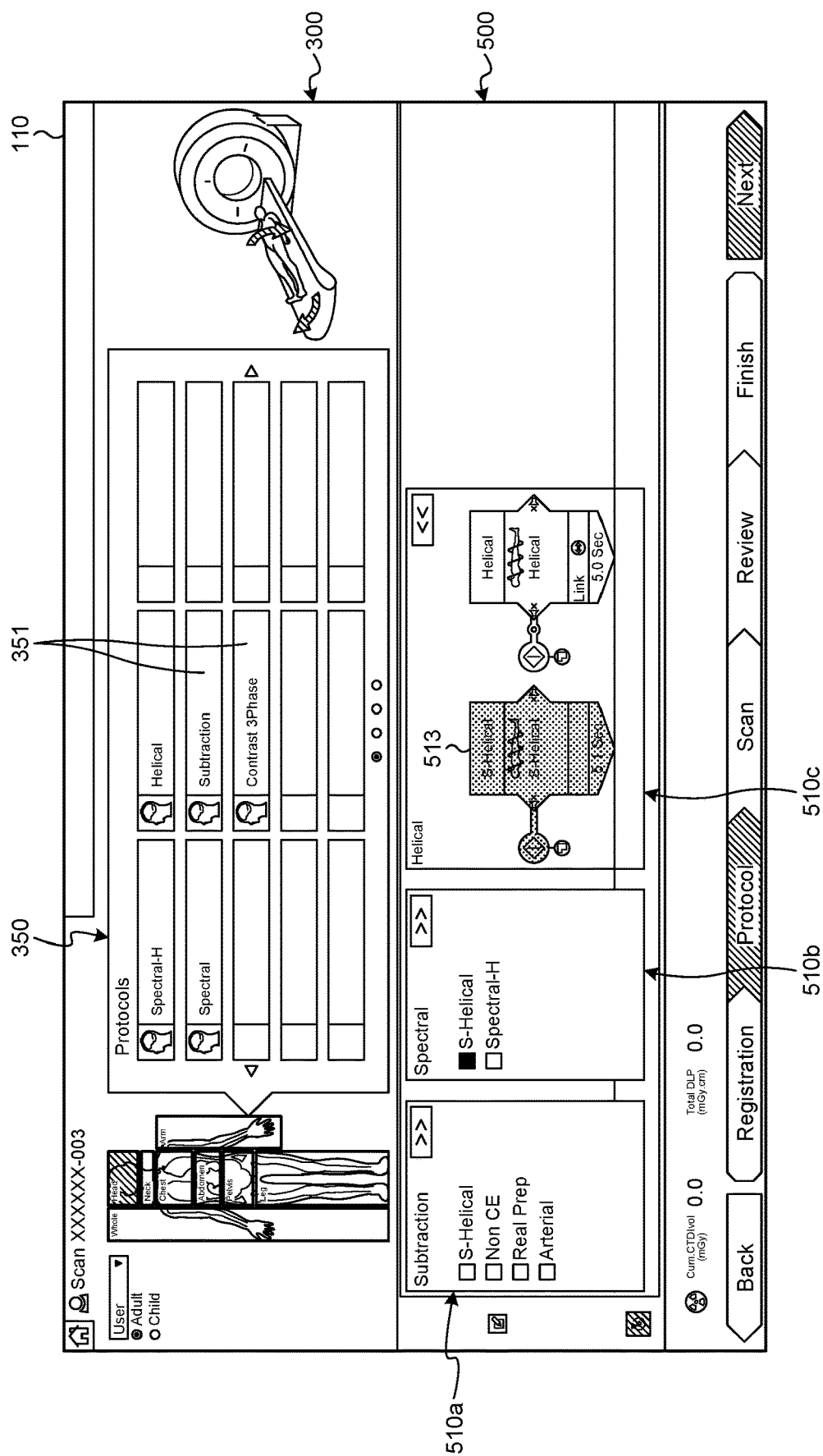
FIG. 6 is a drawing illustrating example (4) of the protocol selecting screen displayed by the display device according to the embodiment.

FIG. 6 is a drawing illustrating example (4) of the protocol selecting screen 110 displayed by the display device 42 according to the embodiment. In the following sections, an example will be explained with reference to FIG. 6 in which the icons 351 of the imaging protocols "Spectral" and "Helical" are further selected on the protocol selecting screen 110 in FIG. 2.

In one example, as explained above with reference to FIG. 5, the operator performs a drag & drop operation on the icons 351 of the imaging protocols "Spectral" and "Helical" which he/she wishes to select, so as to be dropped in the protocol display region 500. On the basis of the input operation received from the operator via the input interface 43, the processing circuit 44 causes the icons 510*b* and 510*c* of the selected protocols to be additionally displayed in the position corresponding to the drop position designated by the operator, within the protocol display region 500.

When the icons 510 of the plurality of selected protocols are displayed in the protocol display region 500 in this manner, the processing circuit 44 may display, as illustrated in FIG. 6, an icon "<<" instructing a collapsed display or an icon ">>" instructing an expanded display of the icons 510 of the selected protocols that are in a collapsed state, together with the icons 510 of the selected protocols.

In one example, the operator may select the icon "<<" instructing the collapsed display. In that situation, as indicated by the icons 510*a* and 510*b* of the selected protocols in FIG. 6, the processing circuit 44 displays the icons 510 of the selected protocols in a collapsed manner. Further, the processing circuit 44 also displays the names of the scans or the like included in the selected protocols that are displayed in the collapsed manner.

In another example, the operator may select the icon "»" instructing the expanded display. In that situation, as indicated by the icon 510*c* of the selected protocol in FIG. 6, the processing circuit 44 displays the icon 510 in the expanded manner. In this situation, the display of the icon 510 in the expanded manner is the same as the display of the icon 510 of the selected protocol illustrated in FIG. 2, for example.

Accordingly, as for the icon 510*c* of the selected protocol in the expanded state, it is possible, as explained above with reference to FIG. 5, to edit the selected protocol in units of protocols or scans, by performing a drag & drop operation, for example.

In contrast, as for the icons 510*a* and 510*b* of the selected protocols in the collapsed state, it is possible to edit the selected protocols in units of protocols, by performing a drag & drop operation, for example. In other words, it is possible to add or insert, to the front and the rear of each of the icons 510 of the selected protocols in the collapsed state, an icon of any of the imaging protocols, of any of the scans included in the imaging protocols, of another selected protocol, or of any of the scans included in the selected protocol in the expanded state. Similarly, the icon 510 of the selected protocol in the collapsed state may be deleted as a whole protocol, may be added or inserted to the front or the rear of the icon 510 of another selected protocol or to a position between the scan icons 513 included in the icon 510 of the selected protocol in the expanded state, or may be replaced with an icon of any of the imaging protocols or of any of the scans included in the imaging protocols.

As explained herein, when the icons 510 of the plurality of selected protocols are displayed in the protocol display region 500, the operator is able to display the icons 510 of the selected protocols by arbitrarily switching between the expanded state and the collapsed state. With this arrangement, the operator is able to easily perform the editing process in units of protocols. Further, because the number of scan icons 513 displayed in the protocol display region 500 is reduced, it is possible to easily understand the entirety of the selected protocols currently displayed.

Figure 7:
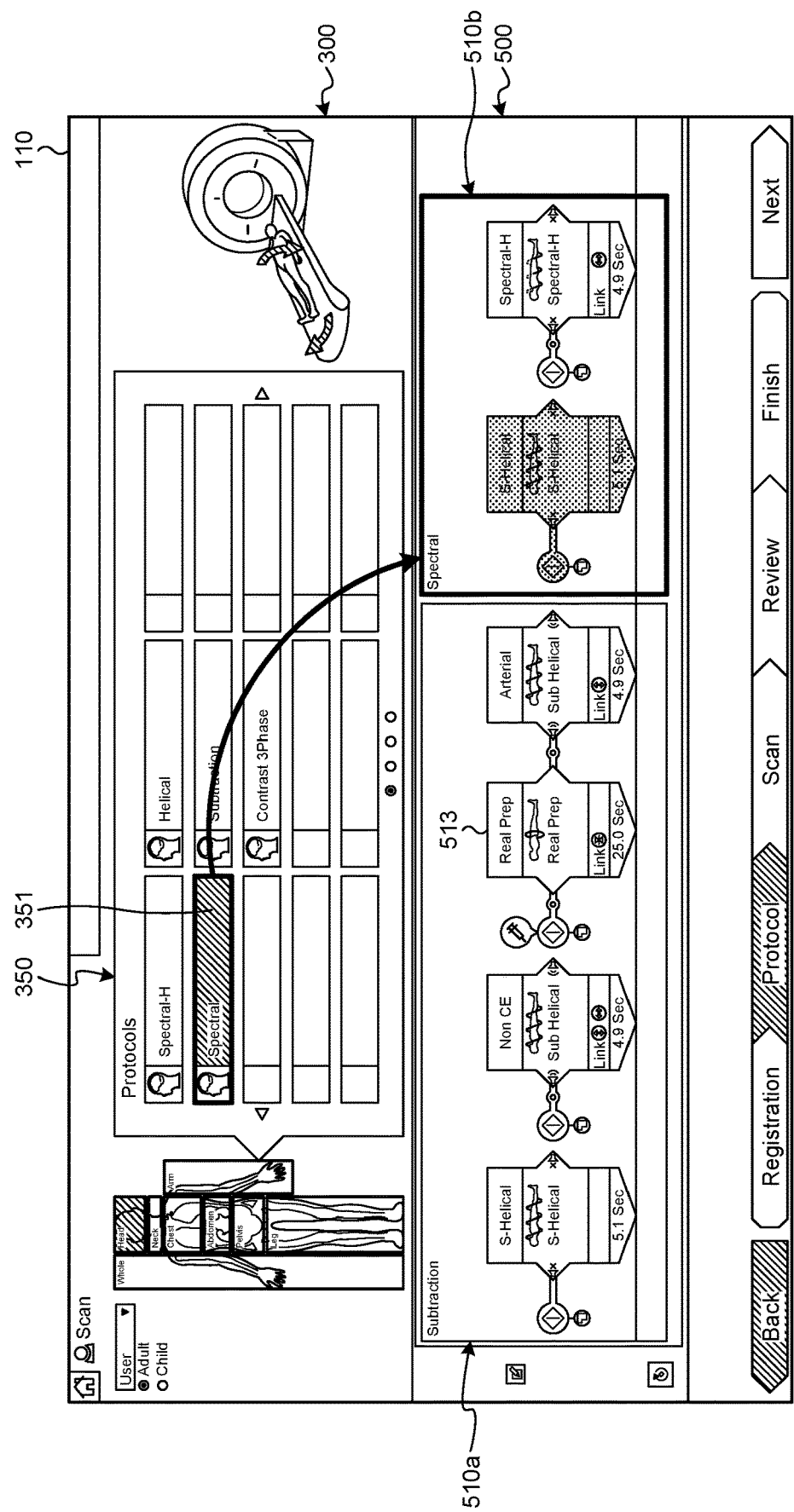
FIG. 7 is a drawing illustrating example (5) of the protocol selecting screen displayed by the display device according to the embodiment.
Figure 8:
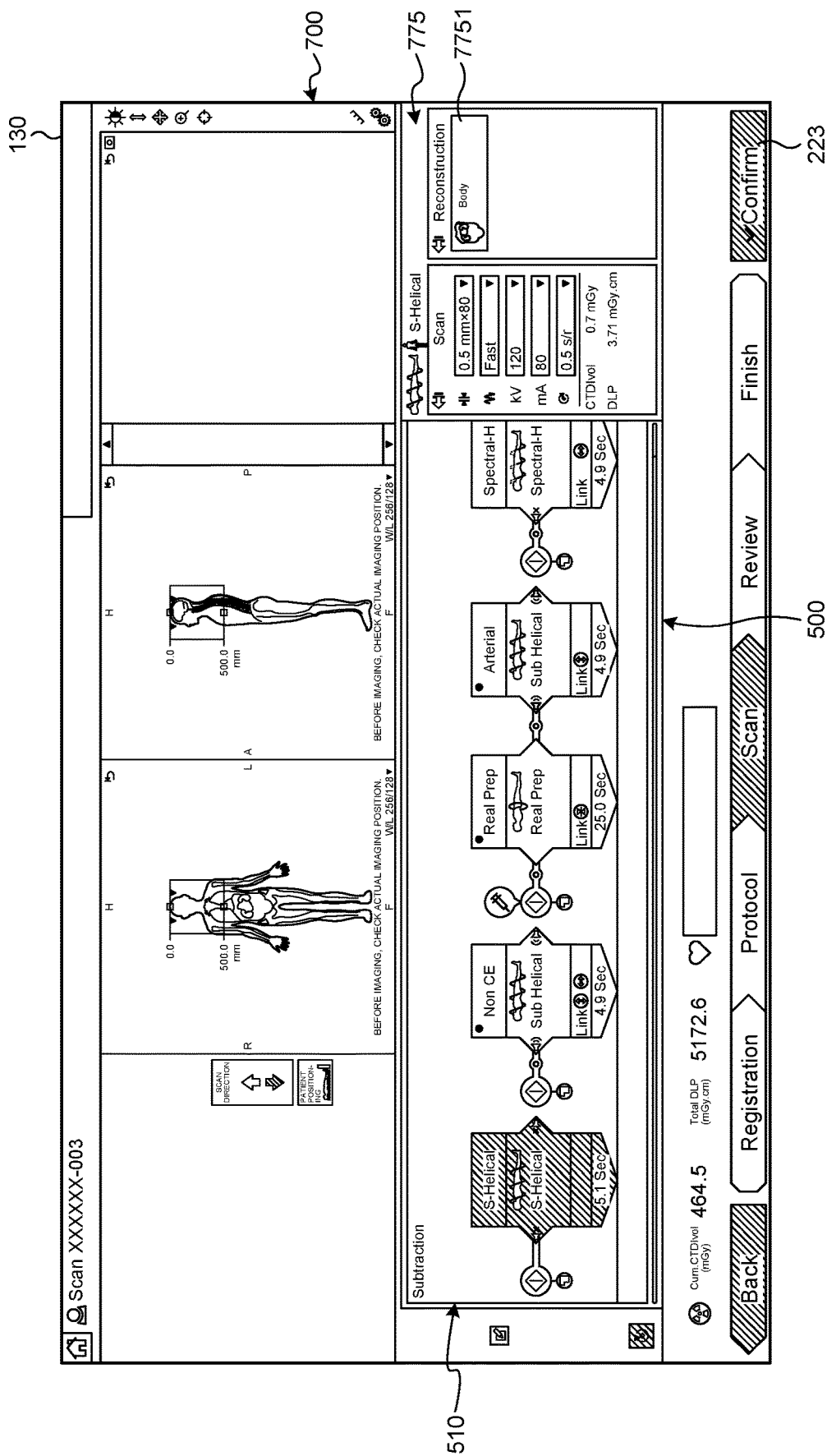
FIG. 8 is a drawing illustrating example (2) of the scan executing screen displayed by the display device according to the embodiment.

FIG. 7 is a drawing illustrating example (5) of the protocol selecting screen 110 displayed by the display device 42 according to the embodiment. FIG. 8 is a drawing illustrating example (2) of the scan executing screen 130 displayed by the display device 42 according to the embodiment.

By performing the editing operation with the drag & drop operation or the like as described above on the icon 510 of the selected protocol currently displayed, it is possible to automatically optimize the scans in the currently-displayed selected protocol.

For example, the position determining imaging process is an element of examinations that is always present within pre-set imaging protocols. For this reason, when the icons 510 corresponding to a plurality of imaging protocols are added or inserted in the protocol display region 500, a plurality of position determining imaging processes are present in the selected protocols.

For example, an imaging protocol for a contrast-enhanced examination may be set, in some situations, with an element of examinations such as a contrast-enhanced imaging protocol or a monitoring scan. Generally speaking, the contrast-enhanced imaging protocol or the monitoring scan is an element of examinations that needs to be performed only once in each examination.

Accordingly, as an automatic optimization process performed on combined selected protocols, the processing circuit 44 is configured to be able to automatically delete one of the scan icons 513 (typically, the second icon and later) representing a duplicate scan, for example.

FIG. 7 illustrates an example in which, on the protocol selecting screen 110 in FIG. 2, the icon 351 of the imaging protocol "Spectral" is further selected. In that situation, as the automatic optimization process, the processing circuit 44 deletes the scan icon 513 of "S-Helical" included in the imaging protocol "Spectral" that is newly selected.

As explained above, within the icon 510 of the selected protocol currently displayed in the protocol display region 500, it is possible to rearrange the scan icons 513. For this reason, in the protocol display region 500 on the protocol selecting screen 110, the processing circuit 44 may display the scan icon 513 of the scan that can be deleted, by using a display mode (e.g., the dot hatching in FIG. 7) indicating that the scan icon 513 represents a scan that can be deleted.

In another example, the processing circuit 44 may display that the scan can be deleted, by increasing the degree of transparency of the scan icon 513, e.g., displaying the scan icon 513 to be translucent. In one example, the processing circuit 44 may display that the scan can be deleted, by displaying the scan icon 513 only with the outline. Further, at the same time as the screen display transitions from the protocol selecting screen 110 to the scan executing screen 130, for example, the processing circuit 44 deletes the scan icon 513 representing the scan that can be deleted. FIG. 8 illustrates the scan executing screen 130 after the transition is made from the protocol selecting screen 110 in FIG. 7. In the example in FIG. 8, as the automatic optimization process, the processing circuit 44 deletes the scan icon 513 of "S-Helical" included in the imaging protocol "Spectral".

Alternatively, the processing circuit 44 may be configured not to display the scan icon 513 of the scan that can be deleted.

Further, in the icon 510 of the selected protocol in the collapsed state, the processing circuit 44 may display that there is a scan that can be deleted. As illustrated in FIG. 6, with respect to the icon 510*b* of the selected protocol in the collapsed state, the processing circuit 44 may display a color-filled box or the like next to the name of a scan included in the selected protocol, for example. In the icon 510*b* of the selected protocol in FIG. 6, a color-filled box is displayed next to the scan name "S-Helical", so as to indicate that this scan can be deleted. In contrast, in the example in FIG. 6, solid white boxes are displayed next to the names of the scans that cannot be deleted, i.e., the scans that are scheduled to be executed.

Further, as a change is made to the icon 510 of the selected protocol currently displayed, the processing circuit 44 may remove the scan that can be deleted from deletion candidates or may change the scan that can be deleted into another scan. For example, when a position determining imaging process that can be deleted is changed into the first position determining imaging process in the currently-displayed selected protocol, the processing circuit 44 removes the position determining imaging scan from deletion candidates. In that situation, if there is, at a later stage, another position determining imaging process that is not designated as a deletion candidate, the processing circuit 44 designates the position determining imaging process as a scan that can be deleted.

When an imaging protocol or an individual scan from another imaging protocol is added or inserted, there may be some situations where values in the settings may be different between the imaging protocols. In those situations, the operator would need to perform operation so as to have details of the conditions loaded onto a scan executing screen and to subsequently return to a setting screen again so as to edit the conditions in order to make the conditions match with those of an imaging protocol or a scan used as a reference.

Under those circumstances, the processing circuit 44 included in the X-ray CT apparatus 1 according to the embodiment is capable of not only optimizing the entirety of the selected protocol currently displayed, but also optimizing the conditions with respect to each of the individual scans. For example, with respect to the entirety of the selected protocol currently displayed in the protocol display region 500, the processing circuit 44 is capable of automatically setting conditions such as an FOV, a table position, and an imaging direction.

However, for example, when a selected protocol is structured by combining an imaging protocol for the head with an imaging protocol for the chest, if the conditions are matched, there is a possibility that a desired image may not be acquired by using only one of the two sets of conditions. In contrast, between an imaging protocol for the chest and an imaging protocol for the abdomen, using the same conditions does not usually cause any problem, in many situations.

Accordingly, the processing circuit 44 is configured to judge whether or not the imaging protocols are of a certain type that allows synchronization and to automatically set (optimize) the conditions with respect to only those imaging protocols that are of a type that allows synchronization. In one example, to judge combinations of imaging protocols, the processing circuit 44 activates a setting where the condition synchronization is turned on or off on the protocol selecting screen 110. In another example, the processing circuit 44 may judge combinations of imaging protocols by referring to judgment data used for making judgment in accordance with the sites of the imaging protocols. In one example, the judgment data may be determined in advance and stored in the memory 41, for example, and may include correspondence relationships between sites and scan conditions as well we threshold values related to whether or not the synchronization is possible. In yet another example, the judgment data may be a machine learning model that has learned a parameter and is configured to receive an input of a site and a scan condition and to output an indication of whether or not the synchronization is possible. In that situation, the parameter of the machine learning model is determined (learned) in advance and stored in the memory 41, for example.

For example, as for imaging protocols having mutually the same site to be imaged, the processing circuit 44 automatically sets the conditions of the later scans, by making the conditions match with the conditions of the scan to be performed first (which may be referred to as a "reference scan"). For example, from a viewpoint of making the image quality uniform, between imaging protocols having mutually-different physiques to be imaged, the processing circuit 44 may make the FOVs of the later scans uniform so as to match with the FOV of the reference scan. Between imaging protocols having mutually-different positionings of the patient P (e.g., having different imaging directions or table positions), the processing circuit 44 automatically sets (optimizes) the conditions.

In contrast, between imaging protocols having mutually-different sites, such as an imaging protocol for the head and an imaging protocol for the chest, the processing circuit 44 is configured not to automatically set (optimize) the conditions.

As explained herein, by automatically setting (optimizing) the conditions between imaging protocols of a certain type that allows the synchronization, it is possible to reduce the operation steps and the time and effort of the operator where the conditions of the imaging protocols are checked so as to make the conditions match with the conditions of the reference scan.

Figure 9:
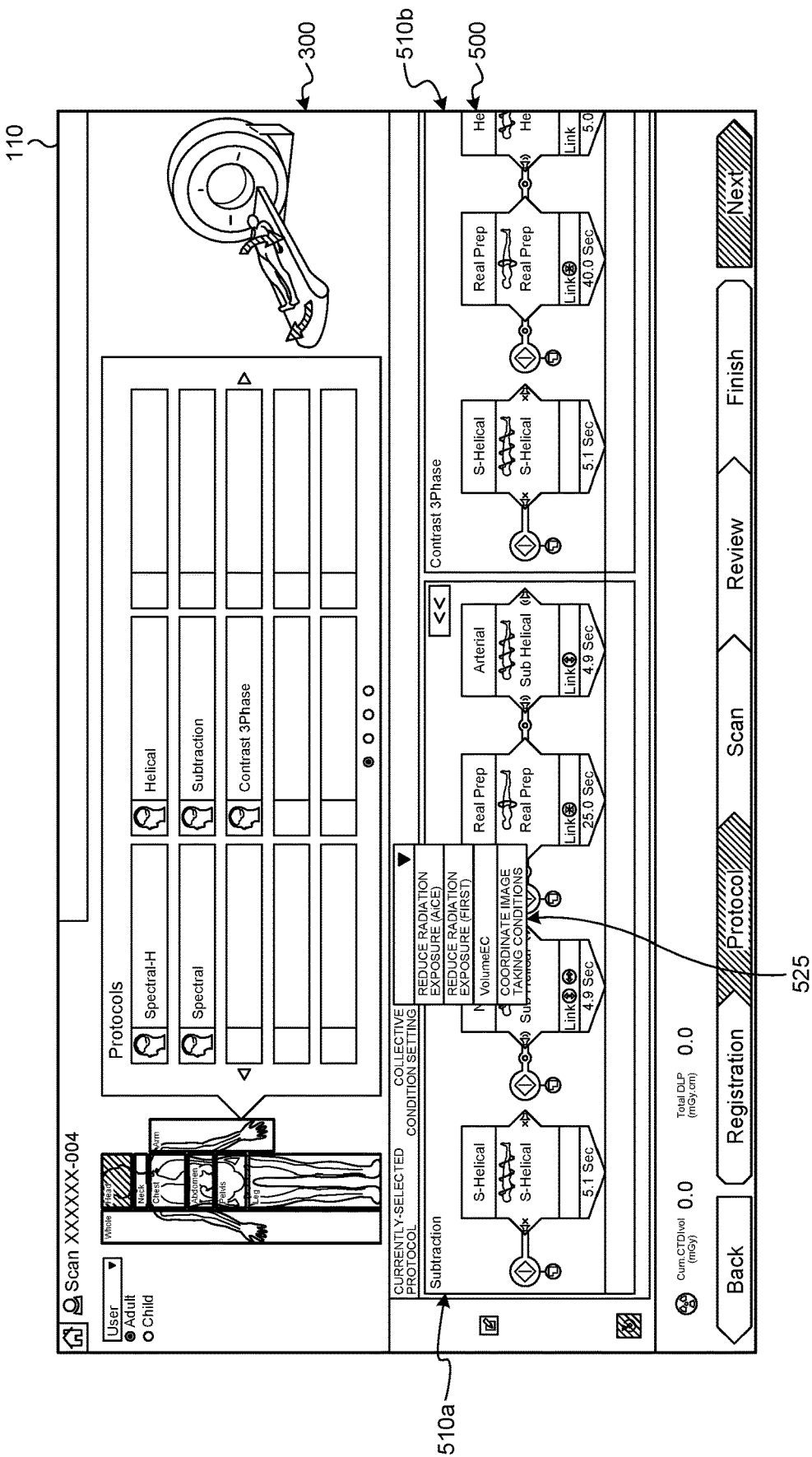
FIG. 9 is a drawing illustrating example (6) of the protocol selecting screen displayed by the display device according to the embodiment.

FIG. 9 is a drawing illustrating example (6) of the protocol selecting screen 110 displayed by the display device 42 according to the embodiment. FIG. 9 illustrates an example in which a collective condition setting process is performed on the protocol selecting screen 110 in FIG. 5.

The example was explained above in which, with respect to the scans indicated in the icon 510 of the selected protocol currently displayed in the protocol display region 500, the conditions are automatically set (optimized) between the imaging protocols of a certain type that allows synchronization. It is, however, also possible to arbitrarily apply a specific condition collectively or by indicating a designation.

In the protocol display region 500, the processing circuit 44 displays, as illustrated in FIG. 9 for example, a collective setting list 525 used for arbitrarily applying a specific condition either collectively or by indicating a designation.

For example, in the protocol display region 500, the operator may select a range of the icon 510 of the selected protocol currently displayed to which the specific condition is to be applied either collectively or by indicating a designation. For example, the operator makes the selection, with a single click, in the icon 510 of the currently-displayed selected protocol to which the specific condition is to be applied. Further, by pulling down the tab "collective condition setting" in the upper part of the protocol display region 500, the operator causes the collective setting list 525 to be displayed and selects one of the conditions he/she wishes to apply. In this situation, when the tab "collective condition setting" is selected while a part or all of the icon 510 of the currently-displayed selected protocol is in an active state, the processing circuit 44 displays the collective setting list 525. Further, when one of the conditions in the collective setting list 525 is selected, the processing circuit 44 applies (revises) the selected condition to the icon 510 of the currently-displayed selected protocol in the active state.

FIG. 9 illustrates an example of the collective setting list 525 displaying conditions such as "Reduce Radiation Exposure (AiCE)", "Reduce Radiation Exposure (FIRST)", "AEC", and "Coordinate Image Taking Conditions". "Reduce Radiation Exposure (AiCE)" and "Reduce Radiation Exposure (FIRST)" are examples of conditions used for the purpose of reducing radiation exposure, which means that a noise reducing process such as the Advance intelligent Clear-IQ Engine (AiCE) or FIRST is carried out together with a reduction in the X-ray tube voltage and the X-ray tube current suitable for the process. "AEC" is an example of conditions used for reducing radiation exposure, where an Automatic Exposure Control (AEC) function is implemented with condition settings thereof. Further, "Coordinate Image Taking Conditions" denotes collectively applying the setting where the condition coordination (synchronization) is turned on or off, similarly to the abovementioned example where the judgment is made on the combinations of the imaging protocols.

Further, the collective setting list 525 may include settings of the subtraction process. For example, in the protocol display region 500, the operator may select "Pre-scan (the icon 510a in FIG. 9)" and "Post-scan (the icon 510b in FIG. 9)" so as to bring these scans into an active state. After that, the operator may set "Subtraction" in the collective setting list 525. As a result, the operator is able to establish a setting with an arbitrary scan currently displayed in the protocol display region 500 so that a subtraction process is to be performed as a post-processing process.

For example, in the example in FIG. 9, both the icon 510a of "Subtraction" and the subsequent icon 510b of "Contrast 3Phase" each include a "Real Prep" scan icon 513. In that situation, when the application of the subtraction process is selected, the processing circuit 44 determines that the "Real Prep" scan included in the selected protocol "Contrast 3Phase" is a scan that can be deleted, as explained above.

Further, when an imaging protocol is generated in advance, in some situations, a radiation exposure amount may be predicted, and an examination time period may also be predicted by totaling scan periods. However, as explained above, when the imaging protocols are combined together or partially deleted in the protocol display region 500, the content of the protocols may have greatly been changed in some situations. To cope with those situations, the processing circuit 44 is configured to display, on the protocol selecting screen 110 for example, a radiation exposure amount and an examination time period resulting from the protocol editing process, with respect to the entirety of the selected protocol currently displayed in the protocol display region 500.

In one example, for single elements or combined elements, the processing circuit 44 is capable of calculating and displaying predicted values of a total scan time period, a total radiation exposure amount, an X-ray tube heat amount, and a time period required by the reconstruction, and/or the like. For example, when a part of the icon 510 of the selected protocol currently displayed in the protocol display region 500 is in the active state by being selected by the operator, the processing circuit 44 may perform the calculation with respect to the selected protocol represented by the icon 510 in the active state.

As a result, without the need to make a transition to the scan executing screen 130, the operator is able to recognize these pieces of information in advance and to use the information as a judgment basis for considering whether or not the selected or edited protocol is suitable for the examination.

Figure 10:
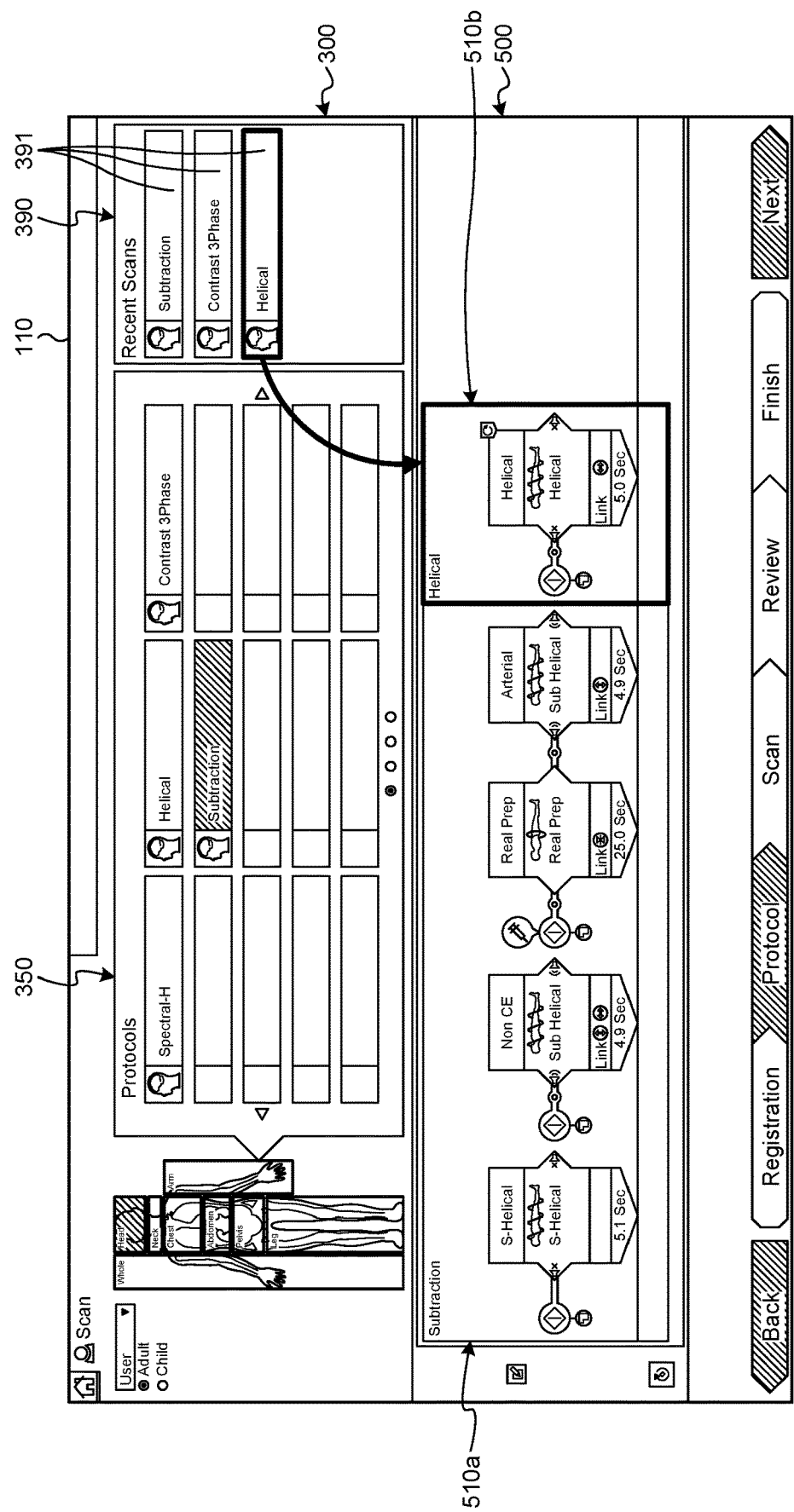
FIG. 10 is a drawing illustrating example (7) of the protocol selecting screen displayed by the display device according to the embodiment.
Figure 11:
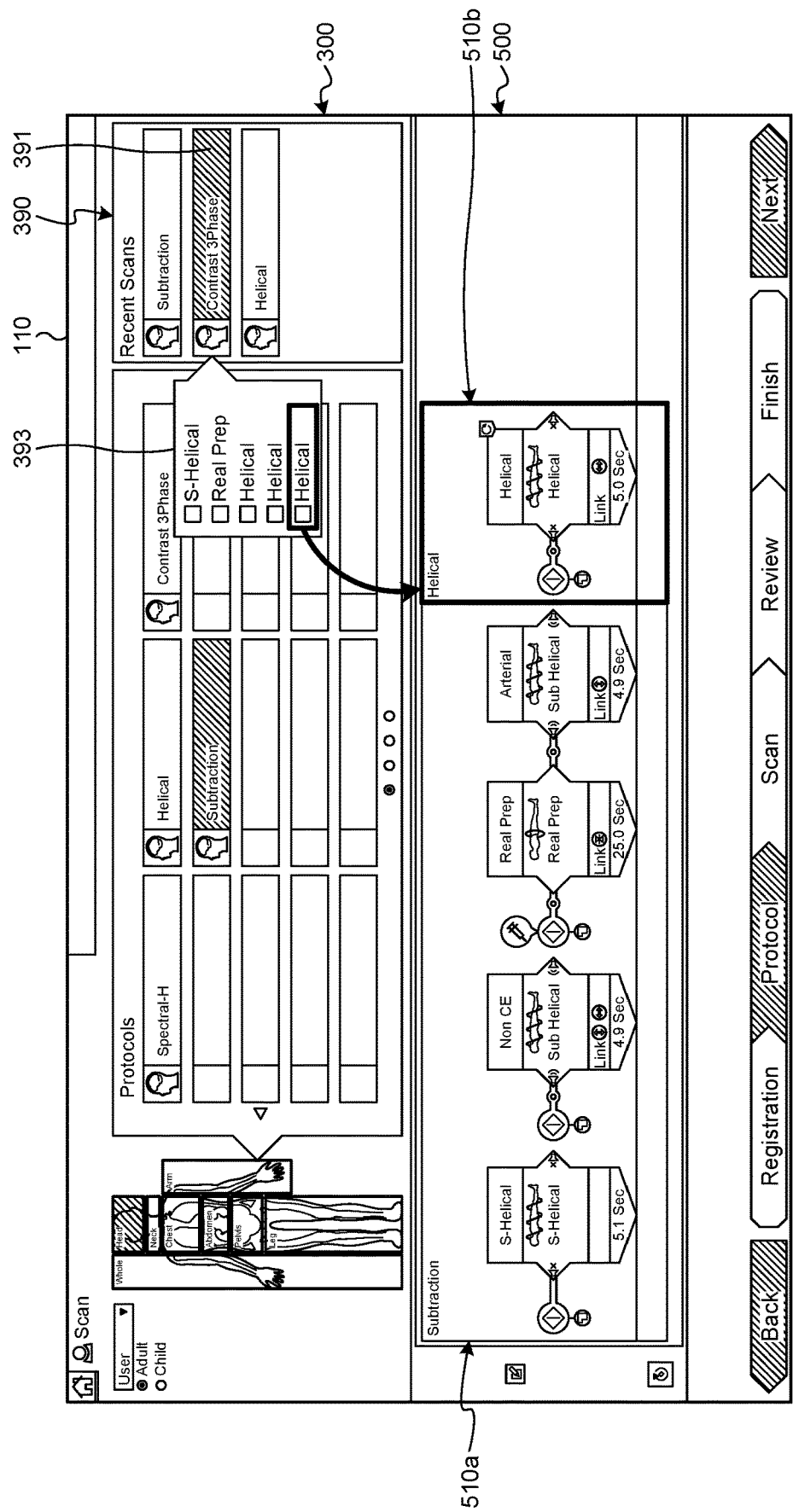
FIG. 11 is a drawing illustrating example (8) of the protocol selecting screen displayed by the display device according to the embodiment.

FIG. 10 is a drawing illustrating example (7) of the protocol selecting screen 110 displayed by the display device 42 according to the embodiment. FIG. 11 is a drawing illustrating example (8) of the protocol selecting screen 110 displayed by the display device 42 according to the embodiment. With reference to FIGS. 10 and 11, examples will be explained in which, on the protocol selecting screen 110 illustrated in FIGS. 2 and 4, respectively, an icon 391 representing the imaging protocol "Helical" is further selected from a history list display region 390.

In the above description, the example of the protocol selecting process is explained in which, by referring to the pre-set imaging protocols in the pre-set list display region 350, an imaging protocol is displayed as the icon 510 of the selected protocol; however, possible embodiments are not limited to this example. It is also acceptable to use an imaging protocol used in the past as a selected protocol.

On the protocol selecting screen 110, the processing circuit 44 is configured to display the history list display region 390. In the history list display region 390, the processing circuit 44 displays, as illustrated in FIG. 10, for example, a history list containing one or more icons 391 of at least one imaging protocol used in the past. In the example in FIG. 10, the history list display region 390 includes the icons 391 of the imaging protocols "Subtraction", "Contrast 3Phase", and "Helical". In another example, as illustrated in FIG. 11, the processing circuit 44 displays, as a scan list 393, icons representing the scans included in the imaging protocol represented by the icon 391 selected from the history list display region 390. In the example in FIG. 11, the scan list 393 contains, similarly to the scan list 353 in FIG. 4, the icons representing the scans "S-Helical", "Real Prep", "Helical", "Helical", and "Helical".

Further, upon completion of the imaging process using the selected protocol displayed in the protocol display region 500 on the scan executing screen 130, the processing circuit 44 is configured to store the selected protocol that was used, into the memory 41, for example, as one of the imaging protocols in the history list display region 390.

In this situation, the pop-up display of the scan list 393 may display only the scan names, similarly to the scan list 353 in FIG. 4 or may use the same display format as the display format used in the protocol display region 500.

For example, similarly to the operation performed on any of the icons 351 of the imaging protocols in the list display region 350 as explained above with reference to FIG. 2 and so on, the operator is able to select any of the icons 391 of the imaging protocols in the history list display region 390. Further, similarly to the operation performed on any of the icons of the scans in the scan list 353 as explained above with reference to FIG. 4 and so on, the operator is able to select any of the scans included in the imaging protocol by using the icons contained in the scan list 393. The same applies to the processes performed by the processing circuit 44.

As explained above, in the protocol editing process performed in the protocol display region 500 with the drag & drop operation and the like, it is possible to easily use any of the imaging protocols and the scans thereof that were used in the past.

Figure 12:
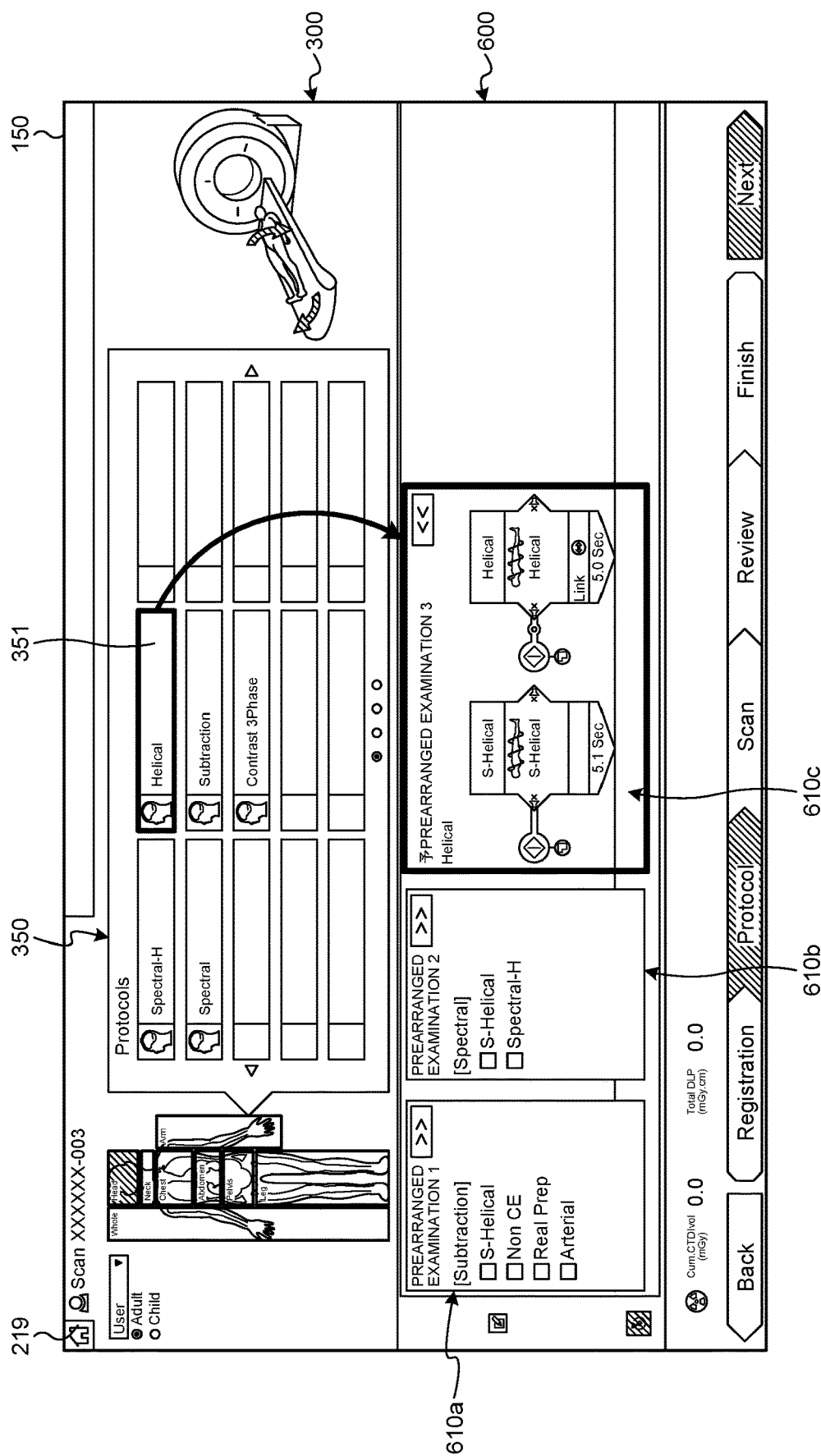
FIG. 12 is a drawing illustrating an example of an examination prearrangement generating screen displayed by the display device according to the embodiment.

FIG. 12 is a drawing illustrating an example of an examination prearrangement generating screen 150 displayed by the display device 42 according to the embodiment.

The techniques related to the protocol editing process performed with the drag & drop operation or the like according to the embodiment are also applicable to generating examination prearrangements 610. In other words, the operator is able to generate the examination prearrangements 610 by selecting an icon 351 of an imaging protocol, similarly to the protocol editing process according to the embodiment.

For example, the operator is able to cause the screen display to transition from the protocol selecting screen 110 to the examination prearrangement generating screen 150, by selecting "examination prearranging process" in a mode setting at "Registration" indicating a patient registration phase in the flow 210 of the examination. Alternatively, the examination prearranging process may be selected by using a menu display that is loaded as a result of the operator selecting a home button 219 displayed in the top left corner of the protocol selecting screen 110 or the scan executing screen 130. Similarly, another arrangement is also acceptable in which the screen display is caused to transition to the protocol selecting screen 110 or the like, as a result of the operator selecting the protocol editing process by using a menu display that is loaded upon selecting the home button 219 displayed in the top left corner of the examination prearrangement generating screen 150.

As illustrated in FIG. 12, on the examination prearrangement generating screen 150, the processing circuit 44 is configured to display the protocol selecting region 300 and an examination prearrangement display region 600. The examination prearrangement display region 600 corresponds to the protocol display region 500 described above. In other words, in the examination prearrangement display region 600, the processing circuit 44 is configured to display icons representing examination prearrangements 610a, 610b, and 610c (610). The icons 610 of the examination prearrangements correspond to the icons 510 of the selected protocols. The processing circuit 44 is configured to display pieces of information representing the elements structuring the imaging protocol such as operations to be performed by the operator and the scans included in the examination prearrangement, so as to be arranged in a time series. In the present example, the examination prearrangement generating screen 150 is an example of the protocol selecting screen. Further, the examination prearrangement display region 600 is an example of the second display region.

In an example, on the examination prearrangement generating screen 150, the operator is able to insert or add, similarly to the protocol editing process described above with reference to FIGS. 2 and 6, the icon 351 of an imaging protocol which he/she wishes to select from the list display region 350 or the history list display region 390 displayed in the protocol selecting region 300, by performing thereon a drag & drop operation or the like so as to be dropped in the examination prearrangement display region 600. The same applies to the processes performed by the processing circuit 44.

In the example in FIG. 12 for instance, as a result of a drag & drop operation, the imaging protocols represented by the three icons 351, namely, "Substraction", "Spectral", and "Helical" are displayed in the examination prearrangement display region 600 as the icons of the examination prearrangements 610a, 610b, and 610c, respectively. Similarly to the icons 510 of the selected protocols, the icons 610 of the examination prearrangements are displayed according to the sequential order of execution. In the example in FIG. 12, the first examination prearrangement (the icon 610a in FIG. 12) is executed first as an examination. When the phase of the examination in the flow 210 of the examination is changed to "Finish", the examination in the second examination prearrangement (the icon 610b in FIG. 12) is automatically started.

Further, the examination prearrangement display region 600 on the examination prearrangement generating screen 150 is configured so that the automatic condition setting process between the examination prearrangements will not be performed, unlike the automatic optimization process on the combined selected protocols described above with reference to FIGS. 6 to 8. In contrast, as explained above with reference to FIG. 9, the operator is able to arbitrarily apply a specific condition collectively or by indicating a designation, to two or more of the examination prearrangements.

In the configuration described above, even when the operator wishes to clearly distinguish the imaging protocols that have been performed from one another, it is possible to add the imaging protocol and to execute the protocols in a distinguished manner, by performing the operation similar to the operation performed when a series of scans included in the displayed icon 510 of the selected protocol are executed as one protocol. Further, although the example with the examination prearrangements was explained above as an example in which the operator wishes to clearly distinguish the executed imaging protocols from one another, this feature is also applicable to situations where the operator wishes to execute the selected protocols displayed in the protocol display region 500 in a distinguished manner.

Further, the protocol editing process using a drag & drop operation or the like according to the embodiment may be applied not only to the protocol selecting screen 110, but also to the scan executing screen 130. In that situation, on the scan executing screen 130, the processing circuit 44 may be configured to realize a display similar to the display of the icons 351 of the imaging protocols and the scan list 353 used for adding the scans thereof, for example. Alternatively, on the scan executing screen 130, the processing circuit 44 may cause the screen display to transition to the protocol selecting screen 110 in response to an operation (a fifth operation input) to select a "Back" button 221 performed by the operator, for example, after a part or all of the scans in the selected protocol displayed in the protocol display region 500. After that, on the protocol selecting screen 110, as explained above, the processing circuit 44 is able to perform the protocol editing process such as adding an imaging protocol (the third imaging protocol) or the scans thereof in response to a drag & drop operation or the like performed by the operator on any of the icons 351.

FIGS. 13 to 16 are drawings illustrating examples (1) to (4), respectively, of a protocol generating screen 170 displayed by the display device 42 according to the embodiment.

In an example, the protocol editing process performed with a drag & drop operation or the like according to the embodiment may be applied to the protocol generating screen 170 used for pre-setting an imaging protocol. In this situation, the protocol generating screen 170 is an operation screen used for generating or revising an imaging protocol to be selected as a selected protocol to be executed on the patient P, on the protocol selecting screen 110 after the information (the patient information) about the patient P has been registered. In the present example, the protocol generating screen 170 is an example of the protocol selecting screen.

Figure 13:
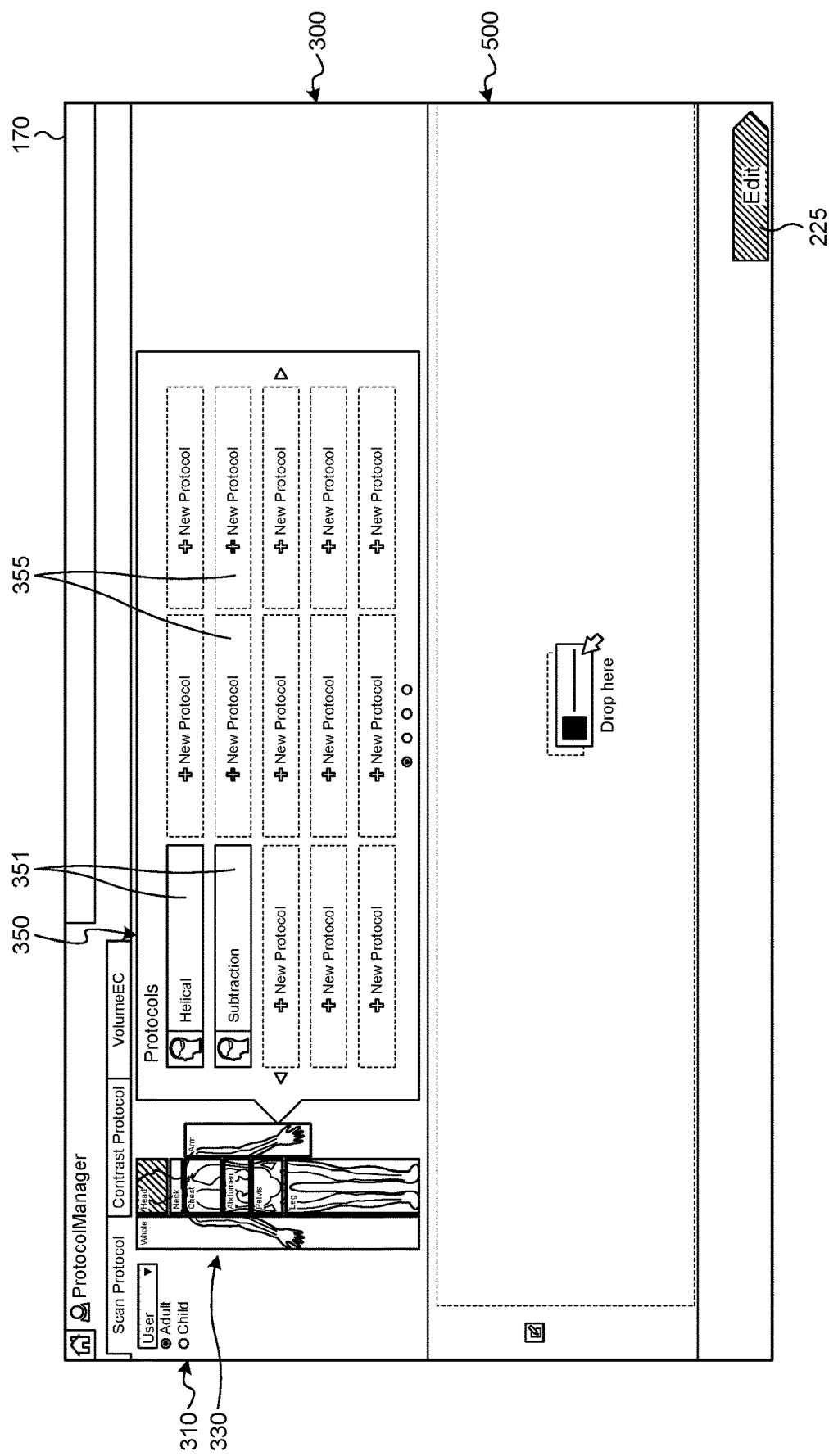
FIG. 13 is a drawing illustrating example (1) of a protocol generating screen displayed by the display device according to the embodiment.
Figure 14:
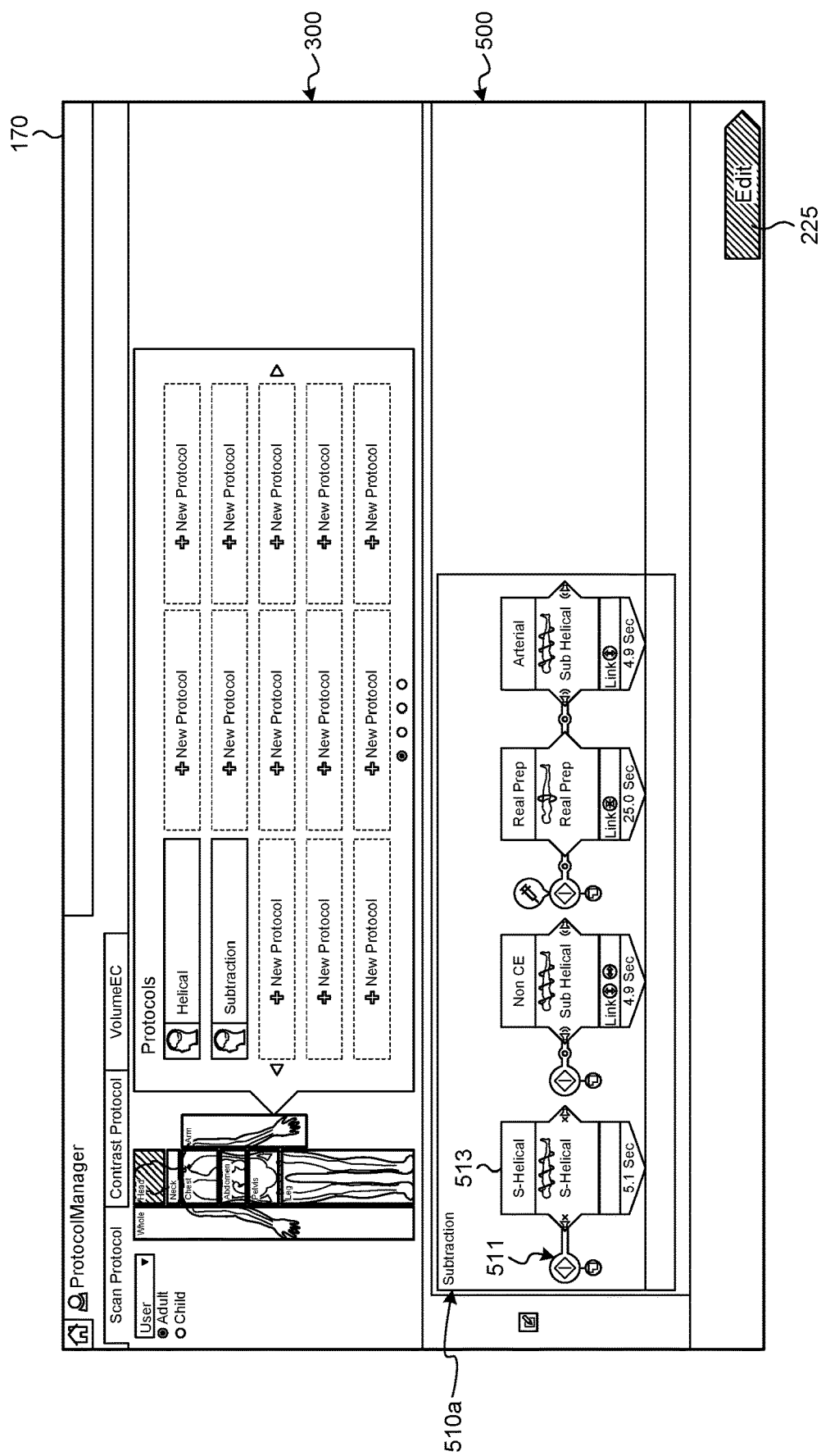
FIG. 14 is a drawing illustrating example (2) of the protocol generating screen displayed by the display device according to the embodiment.
Figure 15:
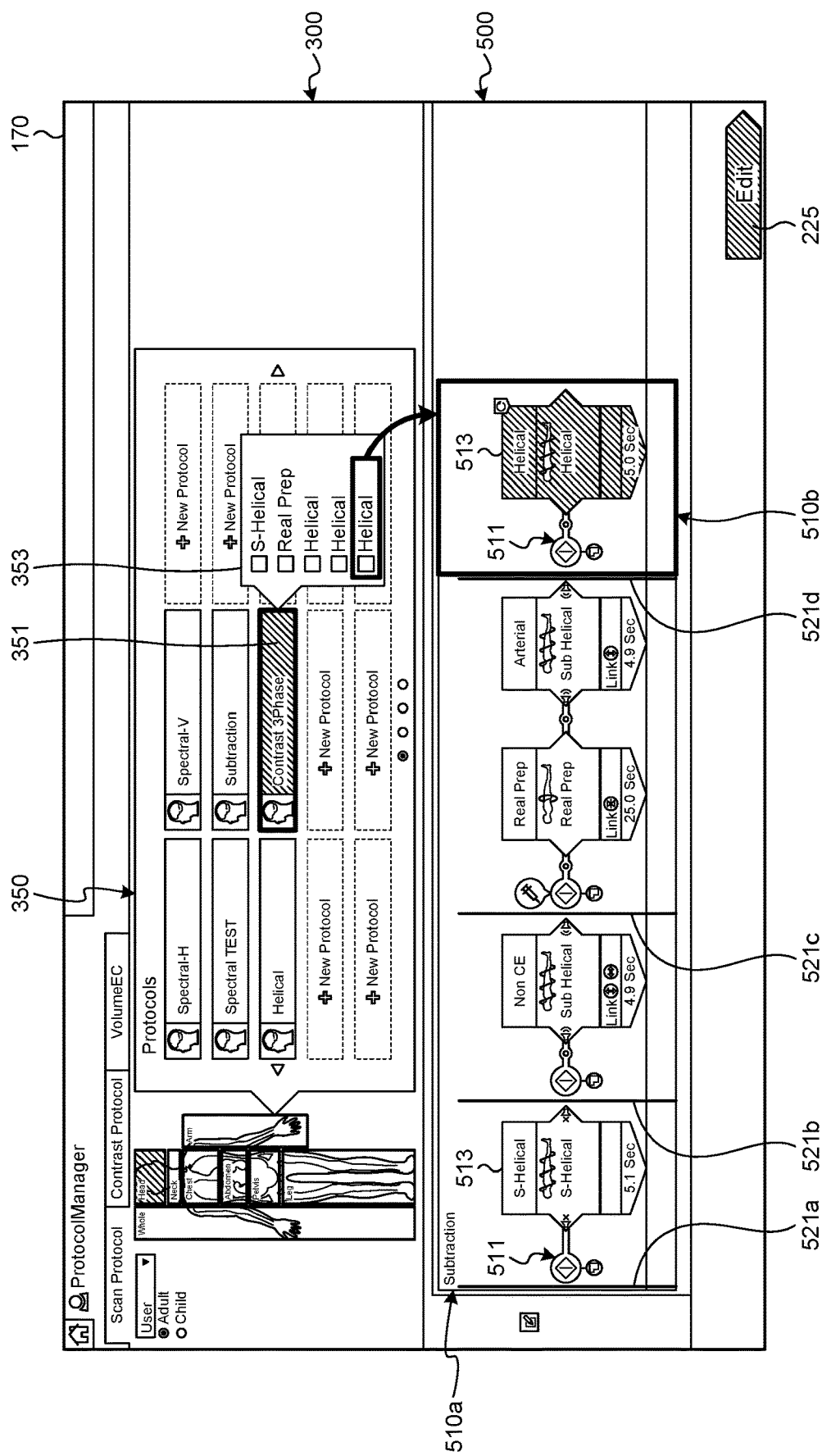
FIG. 15 is a drawing illustrating example (3) of the protocol generating screen displayed by the display device according to the embodiment.
Figure 16:
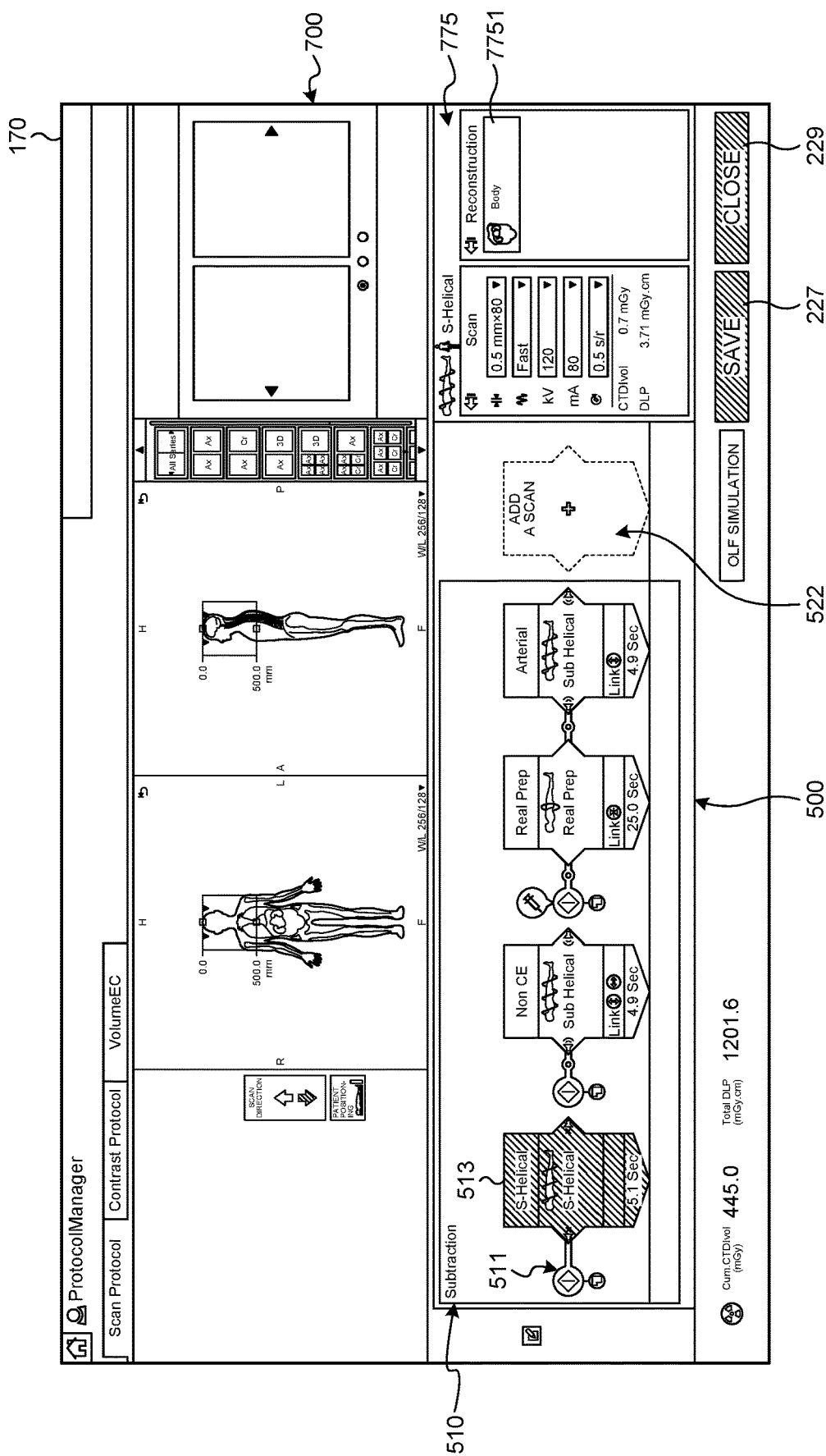
FIG. 16 is a drawing illustrating example (4) of the protocol generating screen displayed by the display device according to the embodiment.

FIG. 13 illustrates an initial state of the protocol generating screen 170. FIGS. 14 and 15 each illustrate a state of the protocol generating screen 170 while displaying protocols. FIG. 16 illustrates a state of the protocol generating screen 170 after a protocol has been read. In this situation, FIGS. 13 to 15 each correspond to the protocol selecting screen 110. On the protocol generating screen 170 in FIGS. 13 to 15, the processing circuit 44 is configured to display the protocol selecting region 300 and the protocol display region 500. Further, FIG. 16 corresponds to the scan executing screen 130. On the protocol generating screen 170 in FIG. 16, the processing circuit 44 is configured to display the protocol display region 500 and the scan information display region 700. In this situation, the operations performed by the operator and the processes performed by the processing circuit 44 on the protocol generating screen 170 are the same as those performed in the protocol editing process described above.

As illustrated in FIG. 13, icons 355 representing new protocols are displayed in the list display region 350. The operator starts a protocol generating process by selecting one of the icons 355 representing a new protocol, for example. In this situation, in response to the operation performed by the operator to select the one of the icons 355 representing a new protocol, the processing circuit 44 identifies, when an imaging protocol is generated as a result of the processes performed thereafter, for example, the display position of the icon 351 of the generated imaging protocol.

As illustrated in FIG. 14, the processing circuit 44 is configured to cause the imaging protocol represented by the icon 351 or the scans thereof selected by an operation performed by the operator to be displayed in the protocol display region 500 as an icon 510 of the selected protocol in the sequential order of execution, in the same manner as in the protocol editing process described above. Further, as illustrated in FIG. 15, the processing circuit 44 may also display the scan list 353 in response to an operation performed by the operator. In addition, the processing circuit may also display icons 521a, 521b, 521c, and 521d in the positions into which an imaging protocol or a scan thereof can be added or inserted.

When the "Edit" button 225 is selected by the operator, the protocol generating screen 170 in FIGS. 14 and 15 transitions to the protocol generating screen 170 in FIG. 16. In response to the operator selecting the "Edit" button 225 while the icon 510 representing the selected protocol is displayed in the protocol display region 500, the processing circuit 44 reads the selected protocol represented by the icon 510 currently displayed in the protocol display region 500 as illustrated in FIG. 16.

On the protocol generating screen 170 in FIG. 16, the operator is able to perform a protocol editing process such as adding, inserting, replacing, or deleting the icon 351 of an imaging protocol, in the same manner as the protocol editing process being performed on the scan executing screen 130 described above. Further, the processing circuit 44 may display an icon 522 indicating s position in which a scan icon 513 can be inserted. Alternatively, in place of the icon 522, the icons 521 may be displayed. In another example, the icon 522 may be displayed on the protocol selecting screen 110 described above.

As explained above, in the protocol display region 500 on the protocol generating screen 170, the content of the protocol is displayed in the same manner as the display on the protocol selecting screen 110 and the scan executing screen 130. Further, similarly to the processes performed on the protocol selecting screen 110 and the scan executing screen 130, the processing circuit 44 is configured, in response to an operation input performed on the protocol display region 500, to change the content displayed in the protocol display region 500 and to also revise the content of the protocol displayed in the protocol display region 500. In another example, in response to an operation input performed to select one of the icons 355 and to generate or edit the content displayed in the protocol display region 500, as appropriate, the processing circuit 44 is able to generate a new protocol.

As explained herein, also in the protocol display region 500 on the protocol generating screen 170, the protocols are visualized in the same manner as on the protocol selecting screen 110 and the scan executing screen 130. It is therefore possible to reduce inadequacies in the settings and the like. Further, it is also possible to easily make revisions on the protocol generating screen 170. As a whole, it is therefore possible to improve the workflow and the throughput.

To register a series of selected protocols represented by the icons 510 currently displayed in the protocol display region 500 as a pre-set of imaging protocols, the operator selects a "Save" button 227. In this situation, in response to the "Save" button 227 being selected, the processing circuit 44 is configured to register the series of selected protocols represented by the icons 510 currently displayed in the protocol display region 500, as the pre-set of imaging protocols to be displayed as icons 351. Further, the operator selects a "Close" button 229 to end the protocol generating process. In this situation, in response to the "Close" button 229 being selected, the processing circuit 44 is configured to end the display of the protocol generating screen 170.

As explained above, by performing the drag & drop operation or the like, the operator is able to easily edit the selected protocol in the protocol display region 500. In other words, it is possible to reduce the operation steps of the operator related to the protocol generating process.

The examples were explained with reference to FIGS. 2 to 16 in which the icon 510 representing the selected protocol is displayed in the protocol display region 500 on the protocol selecting screen 110 and subsequently the transition is made to the scan executing screen 130; however, possible embodiments are not limited to these examples. For instance, on the protocol selecting screen 110, the operator is also able to cause the display screen to transition to the scan executing screen 130, by performing a double-click on the icon 351 of an imaging protocol to be selected or on the icon 510 of the selected protocol currently displayed. In this situation, in response to the double-click operation performed by the operator on the icon 351 representing the imaging protocol or on the icon 510 representing the selected protocol, the processing circuit 44 is configured to cause the display screen to make the transition. As a result, when the operator does not need have information displayed in the protocol display region 500 (e.g., when the operator is aware of the content of the imaging protocol), it is possible to further reduce the time and effort that may be required by the operation input.

Figure 17:
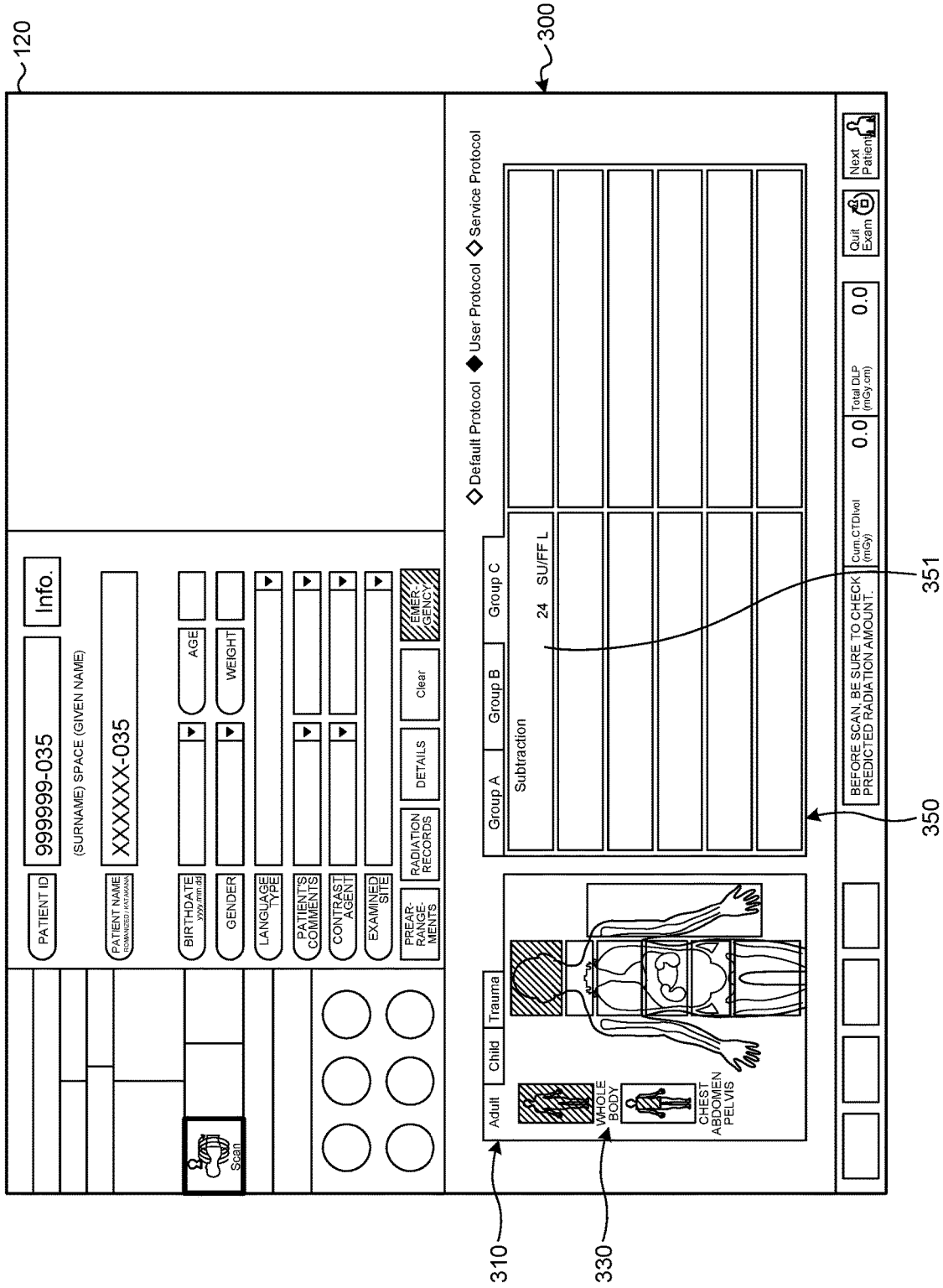
FIG. 17 is a drawing illustrating example (9) of the protocol selecting screen displayed by the display device according to the embodiment.
Figure 18:
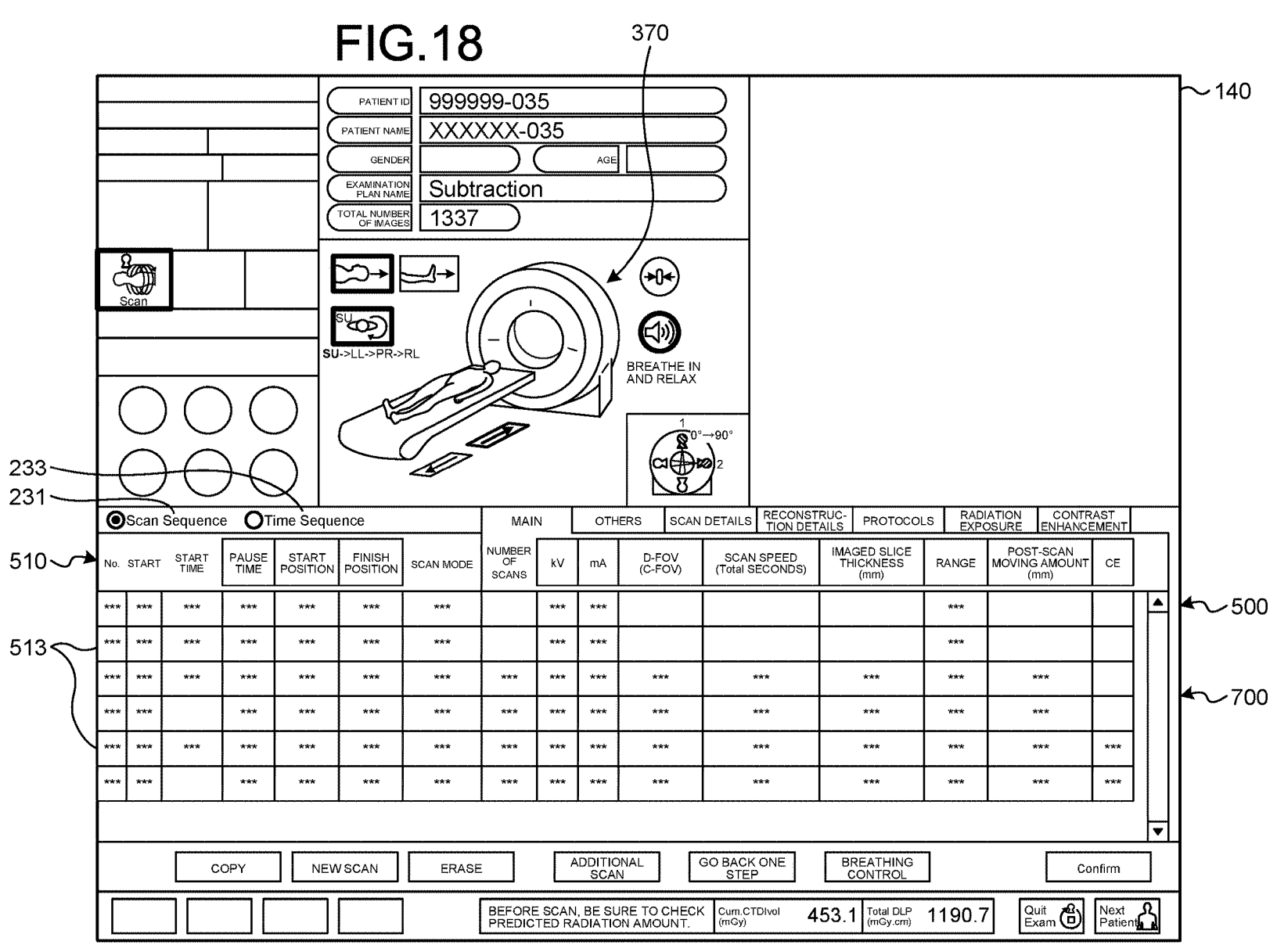

FIG. 17 is a drawing illustrating example (9) of a protocol selecting screen 120 displayed by the display device 42 according to the embodiment. FIG. 18 is a drawing illustrating example (3) of a scan executing screen 140 displayed by the display device 42 according to the embodiment.

On the protocol selecting screen 120, the processing circuit 44 is configured to display the protocol selecting region 300, as illustrated in FIG. 17. However, unlike on the protocol selecting screen 110 illustrated in FIG. 2 and so on, the processing circuit 44 is configure not to display the protocol display region 500. Further, on the scan executing screen 140, the processing circuit 44 is configured to display the protocol display region 500 and the scan information display region 700 as illustrated in FIG. 18. In one example, as illustrated in FIG. 18, the processing circuit 44 displays icons 231 and 233 used for changing display modes of the protocol display region 500 and the scan information display region 700. When "Scan Sequence" represented by the icon 231 is selected, the scans are displayed from the top to the bottom in the sequential order of execution, as illustrated in FIG. 18. When "Time Sequence" represented by the icon 233 is selected, scans executed at different times are displayed in specific time positions on a timeline by using a graph. In the display mode implemented when "Time Sequence" represented by the icon 233 is selected, for example, a vertical axis and a horizontal axis expressing X-ray tube currents [mA] and time on the timeline, respectively, are displayed. On the timeline, the scans are expressed according to the magnitudes of the X-ray tube currents.

On the protocol selecting screen 120 illustrated in FIG. 17, the operator is not able to check the scans included in the imaging protocols or the conditions. For this reason, when the operator wishes to check these types of information, the operator causes the display screen to transition to the scan executing screen 140 illustrated in FIG. 17. Accordingly, when the display screens illustrated in FIGS. 17 and 18 are displayed, it is not possible to reduce the operation steps of the operator, unlike in the protocol editing process described above. However, some operators may prefer using the display screens illustrated in FIGS. 17 and 18, for example, when the operators have previously been using the display screens illustrated in FIGS. 17 and 18 and are familiar with those display screens. Also, for some operators, performing the protocol editing process on the familiar display screen may reduce the number of mistakes or may enhance the operability.

For this reasons, in response to the input operation performed by the operator, for example, the processing circuit 44 according to the present embodiments is configured to be able to switch between the mode in which the protocol editing process is performed on the protocol selecting screen 110 and the scan executing screen 130 illustrated in FIGS. 2, 3, and so on and the mode in which the protocol editing process is performed on the protocol selecting screen 120 and the scan executing screen 140 illustrated in FIGS. 17 and 18, for instance. In one example, in response to an input operation performed by the operator, the processing circuit 44 is configured to cause the display to transition to the protocol selecting screen 120 or the scan executing screen 140 while the protocol selecting screen 110 is displayed, i.e., while a protocol is selected. In another example, the processing circuit 44 is configured to cause the display to transition to the protocol selecting screen 120 or the scan executing screen 140 while the scan executing screen 130 is displayed, i.e., while a scan is executed. In yet another example, the processing circuit 44 is configured to cause the display to transition to the protocol selecting screen 120 or the scan executing screen 140 while the reconstruction is re-tried after the execution of a scan. In addition, for the purpose of reducing risk, the processing circuit 44 is also able to restrict the switching between the modes during the execution of a scan.

In the above-mentioned respective embodiments, there are mainly explained about the protocol editing process, such as adding, inserting, replacing, or deleting an imaging protocol or scan through the protocol selecting screens 110 and 120, the scan executing screens 130 and 140, the examination prearrangement generating screen 150, and the protocol generating screen 170; however, possible embodiments are not limited thereto. The display control related to the protocol editing process according to the above-mentioned respective embodiments can be applied also to a reconstruction condition editing process. It is noted that, as explained above, the imaging protocol includes a scan condition and a reconstruction condition for each of a plurality of scans.

It will be described below about a reconstruction condition editing process according to an embodiment with reference to the scan executing screen 130 as illustrated in FIG. 3, for example.

On the scan executing screen 130, the processing circuit 44 displays the scan information display region 700 including the detailed condition display region 775, as illustrated in FIG. 3. The detailed condition display region 775 includes a reconstruction card 7751 indicating a reconstruction condition. In the example as illustrated in FIG. 3, the reconstruction card 7751 indicating a reconstruction condition is "Brain A". The reconstruction card 7751 of "Brain A" indicates a reconstruction condition corresponding to an imaging protocol named A, which is related to the brain. The reconstruction card 7751 of "Brain A" indicates a reconstruction condition of "OFF" in which no noise reducing process is included.

FIG. 3 illustrates an example of state in which, among the plurality of scan icons 513 currently displayed on the protocol display region 500, a scan icon 513 of "Arterial" is selected in response to an operation input (sixth operation input) from an operator. This operation input is a single click, for example; however, any other operation input may be used. In this situation, the processing circuit 44 displays the one reconstruction card 7751, which is associated with the selected scan icon 513 of "Arterial", as illustrated in FIG. 3. Therefore, in the state illustrated in FIG. 3 as an example, one reconstruction image is generated for raw data obtained from one scan under one reconstruction condition indicated by the one reconstruction card 7751.

In the above circumstances, the raw data may include a plurality of anatomies depending on a site to be imaged. There may be requisition to obtain, for one set of raw data that is obtained from one scan, a plurality of reconstruction images by performing a plurality of reconstructions on the one set of raw data under a plurality of reconstruction conditions. It may be requested for example to obtain, for raw data that is obtained from a scan of the scan, one reconstruction image of soft tissues such as bubbles in the lungs and another reconstruction image of hard tissues such as bones by performing a plurality of reconstructions on the raw data. However, manual inputs of various reconstruction conditions to be newly added may require a lot of time and effort, which may lower the throughput of the image diagnosis process using the medical image diagnosis apparatus.

To solve the problem, on the detailed condition display region 775 (third display region), the processing circuit 44 further displays a new reconstruction card 7752 "+" as illustrated underneath the reconstruction card 7751 of "Brain A", for example. The operator can add a new reconstruction condition using the new reconstruction card 7752 "+".

When the operator selects the new reconstruction card 7752 "+" on the scan executing screen 130, the processing circuit 44 sets a reconstruction condition in accordance with a subsequent operation input from the operator. In addition, the processing circuit 44 displays another reconstruction card 7751 indicating the reconstruction condition newly set at the position of the new reconstruction card 7752 "+".

For example, the operator drags-and-drops the reconstruction card 7751 displayed on the detailed condition display region 775 onto the new reconstruction card 7752 (performs a seventh operation input). In addition, the operator edits a reconstruction condition indicated by the new reconstruction card 7752. In response, the processing circuit 44 copies, to the new reconstruction card 7752, the reconstruction condition indicated by the reconstruction card 7751 dragged-and-dropped onto the new reconstruction card 7752. The processing circuit 44 further edits the reconstruction condition copied to the new reconstruction card 7752 in accordance with the subsequent operation input from the operator and sets the edited reconstruction condition as a new reconstruction condition.

It is noted that the operation input from the operator is not limited to a drag-and-drop operation. The operator, for example, may select the new reconstruction card 7752 "+" and the reconstruction card 7751 displayed on the detailed condition display region 775 each by a single click (seventh operation input). In response, the processing circuit 44 highlights the reconstruction card 7751 selected by the single click and copies the reconstruction condition indicated by the reconstruction card 7751 to the new reconstruction card 7752.

The operation input (seventh operation input) with respect to the display of the reconstruction card 7751 is described in this example, possible embodiments are not limited thereto. For example, the processing circuit 44 may be configured to, in response to an operation input with respect to an image that is obtained from a scanogram imaging (position determining imaging) and displayed on the scan information display region 700 instead of the reconstruction card 7751, cause a reconstruction condition edition executable to add a reconstruction condition associated with the image.

An image that is used instead of the reconstruction card 7751 is not limited to an image that is obtained from a scanogram imaging (position determining imaging). For example, it is acceptable to, in response to an operation input with respect to any type of an image that is obtained from another scan, add a reconstruction condition associated with the image. Moreover, it is acceptable to, in response to an operation input with respect to an image of a reconstruction image, add a reconstruction condition associated with the reconstruction image. Furthermore, it is acceptable to, in response to an operation input with respect to an image previously obtained for the same patient P, add a reconstruction condition associated with the image. Still moreover, it is acceptable to, in response to an operation input with respect to an image previously obtained for another patient P, add a reconstruction condition associated with the image. The processing circuit 44 displays these images on the scan information display region 700, for example.

Alternately, it is acceptable to, in response to an operation input with respect to another imaging protocol or scan, add a reconstruction condition associated with that imaging protocol or scan. In other words, a reconstruction condition may be set by easily applying the reconstruction condition to another scan or imaging protocol.

Still alternately, the processing circuit 44 may be configured to, in response to an operation input with respect to a site of the human body image 790, such as a human body model, a patient's image, or the like instead of the reconstruction card 7751, cause reconstruction condition edition executable to add a reconstruction condition associated with the site, for example.

It is noted that FIG. 3 illustrates, as an example, the case in which the one reconstruction card 7751 that is associated with the scan icon 513 of "Arterial" is displayed on the detailed condition display region 775; however, possible embodiments are not limited thereto. The reconstruction card 7751 displayed on the detailed condition display region 775 may include two or more reconstruction cards 7751.

It is noted that a screen on which the reconstruction condition edition according to an embodiment is performed is not limited to the scan executing screen 130 as illustrated in FIG. 3. The reconstruction condition edition may be executable on each of the above-mentioned screens including the protocol selecting screens 110 and 120, the scan executing screens 130 and 140, the examination prearrangement generating screen 150, and the protocol generating screen 170.

Thus, the medical image diagnosis apparatus according to an embodiment includes the X-ray tube 11 and the X-ray detector 12, the input interface 43, and the processing circuit 44.

The X-ray tube 11 and the X-ray detector 12 image an examined subject. The input interface 43 receives an operation input from an operator.

The processing circuit 44 causes the display 42 to display the protocol generating screen 170 (protocol selecting screen) including the protocol selecting region 300 (first display region) used for displaying the protocol list (list display region 350) indicating the plurality of imaging protocols (icons 351) each including at least one scan and the protocol display region 500 (second display region) used for displaying, in response to a first operation input, the plurality of scan icons 513 representing a plurality of scans selected from the plurality of imaging protocols (icons 351) and being arranged in a sequential order of execution.

The processing circuit 44 causes, in response to a third operation input, a display screen displayed by the display 42 to transition from the protocol generating screen 170 (protocol selecting screen) to the scan executing screen 130 that includes the protocol display region 500 (second display region) and is used for executing the plurality of scans as one imaging protocol (icon 510) in the sequential order corresponding to the plurality of scan icons 513 displayed in the protocol display region 500 (second display region).

The scan executing screen 130 includes the detailed condition display region 775 (third display region) used for displaying, in response to a sixth operation input to select a scan to be edited from the plurality of scans in the protocol display region 500 (second display region), the reconstruction card 7751 indicating a reconstruction condition that is associated with the scan to be edited and the new reconstruction card 7752 indicating addition of a new reconstruction condition.

The processing circuit 44 sets, in response to a seventh operation input with respect to the reconstruction card 7751 and the new reconstruction card 7752, a new reconstruction condition based on the reconstruction condition indicated by the reconstruction card 7751.

With this configuration, the operator can easily add a reconstruction condition by editing the reconstruction condition indicated by the reconstruction card 7751 copied. In other words, the operator can perform, by means of easy adjustment of another reconstruction condition, a plurality of reconstructions on raw data that is obtained from one scan under a plurality reconstruction conditions to obtain a plurality of reconstruction images.

The term "processor" used in the above explanations denotes, for example, a Central Processing Unit (CPU), a Graphics Processing Unit (GPU), or a circuit such as an ASIC or a Programmable Logic Device (PLD). Examples of the PLD include a Simple Programmable Logic Device (SPLD), a Complex Programmable Logic Device (CPLD), and a Field Programmable Gate Array (FPGA). One or more processors realize the functions by reading and executing the programs saved in a storage circuit. The storage circuit saving the programs therein is a non-transitory computer-readable recording medium. Further, instead of saving the programs in the storage circuit, it is also acceptable to directly incorporate the programs into the circuits of the processors. In that situation, the processors realize the functions by reading and executing the programs incorporated in the circuits thereof. Further, instead of executing the programs, it is also acceptable to realize the functions corresponding to the programs by using a combination of logic circuits. Further, the processors of the present embodiments do not each necessarily have to be structured as a single circuit. It is also acceptable to structure one processor by combining together a plurality of independent circuits so as to realize the functions thereof. Further, it is also acceptable to integrate two or more of the constituent elements illustrated in FIG. 1 in one processor so as to realize the functions thereof.

According to at least one aspect of the embodiments described above, it is possible to improve the throughput of the image diagnosis process using the medical image diagnosis apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus, comprising:
an X-ray tube and an X-ray detector configured to image an examined subject;
input interface hardware configured to receive various operation inputs from an operator; and
processing circuitry configured to:
cause a display to display a protocol selecting screen including a first display region used for displaying a protocol list indicating a plurality of imaging protocols each including at least one scan, and a second display region used for displaying, in response to a first operation input of the operation inputs, a plurality of icons representing a plurality of scans selected from the plurality of imaging protocols and being arranged in a sequential order of execution,
change, when a scan condition of the plurality of scans in the second display region is revised in response to a second operation input of the operation inputs, the display of the plurality of icons in accordance with the revised scan condition,
cause, in response to a third operation input of the operation inputs, a display screen displayed by the display to transition from the protocol selecting screen to a scan executing screen that includes the second display region and is used for executing the plurality of scans as one imaging protocol in the sequential order corresponding to the plurality of icons displayed in the second display region, and
revise the scan condition in response to the second operation input and control the imaging of the examined subject in accordance with the imaging protocol displayed in the second display region on the scan executing screen.

2. The medical image diagnosis apparatus according to claim 1, wherein
while the protocol selecting screen is displayed, when the first operation input is performed on a first imaging protocol contained in the protocol list in the first display region, the processing circuitry is further configured to cause an icon representing a scan included in the first imaging protocol to be displayed in the second display region on the protocol selecting screen, and
while the protocol selecting screen is displayed, when the third operation input is performed on the first imaging protocol, the processing circuitry is further configured to cause a display screen displayed by the display to transition to the scan executing screen used for executing the first imaging protocol and causes cause the icon representing the scan included in the first imaging protocol to be displayed in the second display region on the scan executing screen.

3. The medical image diagnosis apparatus according to claim 1, wherein
while the protocol selecting screen is displayed, when the first operation input is performed on a first imaging protocol contained in the protocol list in the first display region, the processing circuitry is further configured to cause an icon representing a scan included in the first imaging protocol to be displayed in the second display region on the protocol selecting screen, and while the protocol selecting screen is displayed, when a fourth operation input of the operation inputs is performed on the first imaging protocol, the processing circuitry is further configured to cause a scan list indicating one or more scans included in the first imaging protocol to be displayed in the first display region on the protocol selecting screen.

4. The medical image diagnosis apparatus according to claim 1, wherein, while an icon representing a scan included in a first imaging protocol contained in the protocol list within the first display region is displayed in the second display region on the protocol selecting screen, when the first operation input is performed on a second imaging protocol contained in the protocol list in the first display region, the processing circuitry is further configured to cause an icon representing a scan included in the second imaging protocol to be displayed in a position that corresponds to content of the first operation input and is in the second display region on the protocol selecting screen.

5. The medical image diagnosis apparatus according to claim 1, wherein the first operation input is a drag-and-drop operation.

6. The medical image diagnosis apparatus according to claim 1, wherein, in response to the second operation input, the processing circuitry is further configured to collectively revise scan conditions respectively related to the plurality of scans corresponding to the plurality of icons displayed in the second display region.

7. The medical image diagnosis apparatus according to claim 1, wherein
while the scan executing screen is displayed before the imaging protocol displayed in the second display region is completed, the processing circuitry is further configured to cause the display screen displayed by the display to transition from the scan executing screen to the protocol selecting screen in response to a fifth operation input of the operation inputs,
while the protocol selecting screen is displayed, when the first operation input is performed on a third imaging protocol contained in the protocol list in the first display region, the processing circuitry is further configured to cause an icon representing a scan included in the third imaging protocol to be displayed in a position that corresponds to content of the first operation input and is in the second display region on the protocol selecting screen, and
the processing circuitry is further configured to cause one or more scans included in the third imaging protocol displayed in the second display region to be executed in a sequential order corresponding to display positions in the second display region.

8. The medical image diagnosis apparatus according to claim 1, wherein
the processing circuitry is further configured to cause a protocol generating screen to be displayed, which is used for setting content of a protocol displayed in the first display region,
the protocol generating screen has a display region in which an existing protocol is displayed in a same manner as a manner used in the second display region on the protocol selecting screen, and
in response to an operation input of the operation inputs performed on the display region, the existing protocol is revised.

9. The medical image diagnosis apparatus according to claim 1, wherein
the processing circuitry is further configured to:
cause the display to display, in response to a sixth operation input of the operation inputs to select a scan to be edited from the plurality of scans in the second display region, the scan executing screen that includes a third display region used for displaying a reconstruction card indicating a reconstruction condition that is associated with the scan to be edited and a new reconstruction card indicating addition of a new reconstruction condition, and
set, in response to a seventh operation input of the operation inputs with respect to the reconstruction card and the new reconstruction card, a new reconstruction condition based on the reconstruction condition indicated by the reconstruction card.

10. The medical image diagnosis apparatus according to claim 3, wherein, when the first operation input is performed to select one of the scans from the scan list, the processing circuitry is further configured to cause an icon representing the scan selected from the scan list to be displayed in the second display region on the protocol selecting screen.

11. The medical image diagnosis apparatus according to claim 4, wherein
the first operation input is a drag-and-drop operation, and
the content of the first operation input is a drop position in the drag-and-drop operation.

12. The medical image diagnosis apparatus according to claim 4, wherein, in accordance with the content of the first operation input, the processing circuitry is further configured to replace the icon representing the scan included in the first imaging protocol, with an icon representing a scan included in the second imaging protocol.

* * * * *